US007482353B2

(12) United States Patent
Bhattacharya et al.

(10) Patent No.: US 7,482,353 B2
(45) Date of Patent: Jan. 27, 2009

(54) COMPOSITIONS AND METHODS PERTAINING TO PNA SYNTHONS AND OLIGOMERS COMPRISING A UNIVERSAL BASE

(75) Inventors: Birendra K. Bhattacharya, Kent, OH (US); James M. Coull, Westford, MA (US)

(73) Assignee: Applied Biosystems Inc., Foster City, CA (US)

( * ) Notice: Subject to any disclaimer, the term of this patent is extended or adjusted under 35 U.S.C. 154(b) by 38 days.

(21) Appl. No.: 11/452,443

(22) Filed: Jun. 14, 2006

(65) Prior Publication Data

US 2006/0287526 A1    Dec. 21, 2006

Related U.S. Application Data

(60) Provisional application No. 60/690,569, filed on Jun. 15, 2005.

(51) Int. Cl.
*A01N 43/90* (2006.01)
*A61K 31/519* (2006.01)

(52) U.S. Cl. .................................. 514/262.1
(58) Field of Classification Search .................. 544/262
See application file for complete search history.

(56) References Cited

U.S. PATENT DOCUMENTS

| 6,133,444 | A | 10/2000 | Coull et al. |
| 6,172,226 | B1 | 1/2001 | Coull et al. |
| 6,433,134 | B1 | 8/2002 | Patron et al. |
| 2004/0162282 | A1 | 8/2004 | Pennell et al. |

FOREIGN PATENT DOCUMENTS

| WO | WO00/02899 | 1/2000 |
| WO | 02/14277 | 2/2002 |
| WO | WO03/105853 | 12/2003 |

OTHER PUBLICATIONS

Avasthi, et al., European Journal of Medicinal Chemistry (1993), 28(7-8), 585-91.*
Challa, H. et al, "Nitroazole Universal Bases in Peptide Nucleic Acids", Organic Letters, 1999 vol. 1, No. 10, pp. 1639-1641, American Chemical Society.
El Fanham, H., "Synthesis of Some New Pyrazoloazole and Pyrazoloazine Derivatives", Egypt. J. Pharm. Sci. vol. 33, No. 3-4, pp. 561-570 (1992).
Elnagdi, Mohamed Hilmy, et al, "Reactions with Hereocyclic Amidines VIII. Synthesis of some New Imidazo [1,2-b]pyrazole Derivatives", Journal of Heterocyclic Chemistry, 17 (1) pp. 73-76 (1980).
Kohler O. et al, "Forced Intercalation Probes (FIT Probes) : Thiazole Orange as a Fluorescent Base in Peptide Nucleic Acids for Homogeneous Single-Nucleotide-Polymorphism Detection", ChemBioChem Full Papers, 2005, 6, pp. 69-77.

(Continued)

*Primary Examiner*—James O. Wilson
*Assistant Examiner*—Jeffrey H Murray
(74) *Attorney, Agent, or Firm*—Brian D. Gildea; Shirley A. Récipon

(57) ABSTRACT

This invention is related to compositions and methods pertaining to PNA synthons, PNA oligomers and/or PNA/DNA Chimeras comprising a universal base.

18 Claims, 11 Drawing Sheets

OTHER PUBLICATIONS

Oliver, J. et al, "Characterizing Universal Bases for Hybridization Dependent Processes: Betting on Wildcards for Sequencing by Hybridization", Abstract of Papers, 222$^{nd}$ ACS National Meeting, Chicago, IL, Aug. 26-30 (2001).

Robins, R., "Potential Purine Antagonists. I. Synthesis of Some 4,6-Substituted Pyrazolo [3,4-d]pyrimidines[1]", Journal of American Chemical Society, vol. 78, pp. 784-790 (1955).

Seela, F. et al, "The N$^8$-(2'-deoxyribofuranoside) of 8-aza-7-deazaadenine: a universal nucleoside forming specific hydrogen bonds with the four canonical DNA constituents", Nucleic Acids Research, 2000, vol. 28, No. 17, pp. 3224-3232.

Seela, F. et al, "Base Pairing Properties of 8-Aza-7-deazaadenine Linked via the 8-Position to the DNA Backbone" Helvetica. Chem. Acta, 2000, 83, 1437.

Seela, F. et al, "8-Aza-7-deazaadenine N8-and N9-(β-D-2'-Deoxyribofuranosides): Building Blocks for Automated DNA-Synthesis and Properties of Oligodeoxyribonucleotides" Helvetica Chem. Acta, 1988, 71, 1813.

Seitz, O., "Convergent Strategies for the Attachment of Fluorescing Reporter Groups to Peptide Nucleic Acids in Solution and on Solid Phase", Chem. Eur. Journal, 2001, 7, No. 18, pp. 3911-3925.

Seitz, O., "A Convergent Strategy for the Modification of Peptide Nucleic Acids: Novel Mismatch-Specific PNA-Hybridization Probes", Angewadte Chem. Int. Ed., 1999, 38, No. 15, pp. 2203-2206.

Thomson, S., et al, "Fmoc Mediated Synthesis of Peptide Nucleic Acids", Tetrahedron, 51(22) : 6179-6194 (1995).

Zhang, P. et al, "Peptide Necleic Acid-DNA Duplexes Containing the Universal Base 3-Nitropyrrole", Methods, 23, pp. 132-140.

Larsen et al., "Synthesis and Biological Activity of Analogues of the Antidiabetic/Antiobesity Agent 3-Guanidinopropionic Acid: Discovery of a Novel Aminoguanidinoacetic Acid Antidiabetic Agent", J. Med. Chem., Apr. 12, 2001, vol. 44, pp. 1217-1230.

International Search Report and Written Opinion of the International Searching Authority, or the Declaration from the counter-part application PCT/US06/23293, mailed Jun. 11, 2008.

* cited by examiner

COMPOSITIONS AND METHODS PERTAINING TO PNA SYNTHONS AND OLIGOMERS COMPRISING A UNIVERSAL BASE

CROSS REFERENCE TO RELATED APPLICATIONS

This application claims priority to U.S. provisional application No. 60/690,569 filed Jun. 15, 2005.

The section headings used herein are for organizational purposes only and are not to be construed as limiting the subject matter described in any way.

1. FIELD

This invention is related to the field of the organic synthesis of nucleobases and their incorporation into synthons and oligomers.

2. INTRODUCTION

Peptide nucleic acid is a class of synthetic nucleobase comprising oligomers that can sequence specifically hybridize to nucleic acids and other polynucleobase strands. Hybridization between nucleobases of polynucleobase strands typically follows well-established rules for hydrogen bonding. For Watson-Crick base pairing, typically adenine base pairs with thymine and cytosine base pairs with guanine.

A nucleoside comprising the nucleobase 8-aza-7-deazaadenine has been investigated and found to exhibit properties of a universal nucleoside (Seela et al. *Nucl. Acids Res.*, 28(17): 3224-3232 (2000). The term universal nucleoside refers to a nucleoside that forms specific hydrogen bonds towards the four canonical DNA nucleobases (i.e. adenine, thymine, cytosine and quanine). It would be useful to have methods for the preparation of PNA synthons and PNA oligomers comprising a universal nucleobase such as 8-aza-7-deazaadenine.

3. DRAWINGS

The skilled artisan will understand that the drawings, described below, are for illustration purposes only. The drawings are not intended to limit the scope of the present teachings in any way.

Figure 5:
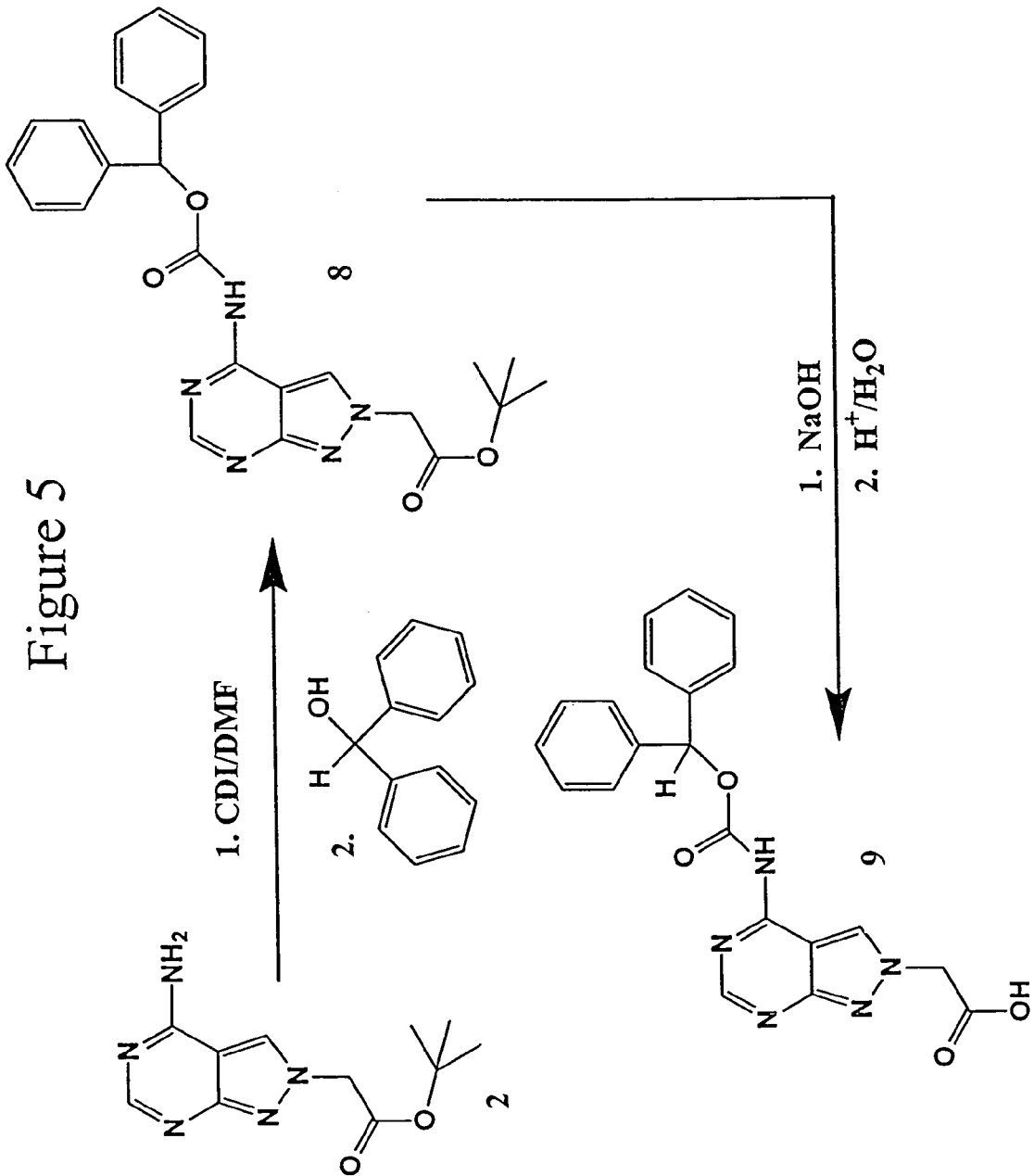

FIG. 5 provides an illustration of a synthetic route to a Bhoc protected N8-alkylated 8-aza-7-deazaadenine nucleobase.

Figure 6:
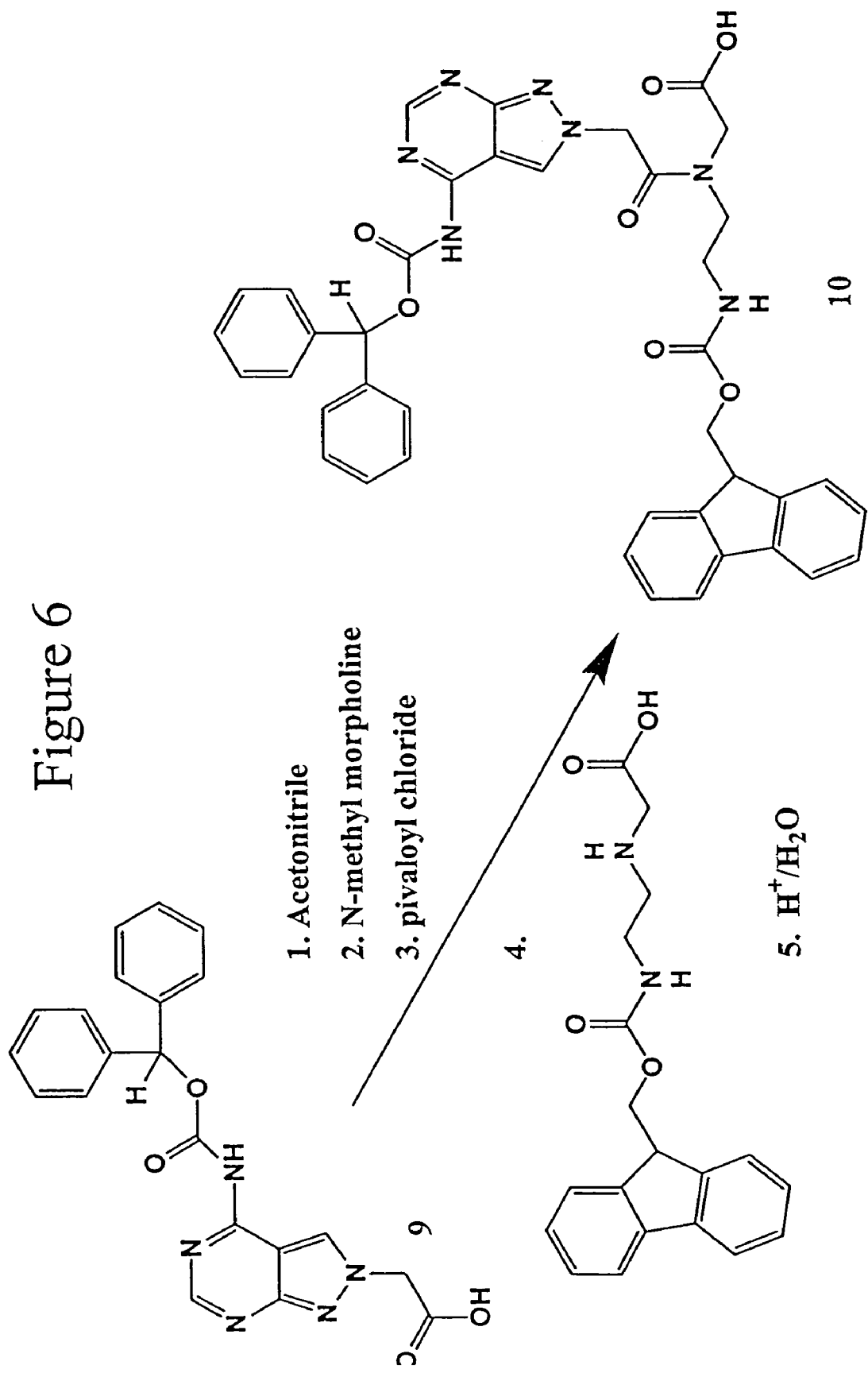

FIG. 6 illustrates a synthetic route to an Fmoc/Bhoc protected PNA monomer comprising a protected N8-alkylated 8-aza-7-deazaadenine nucleobase.

Figure 7A:
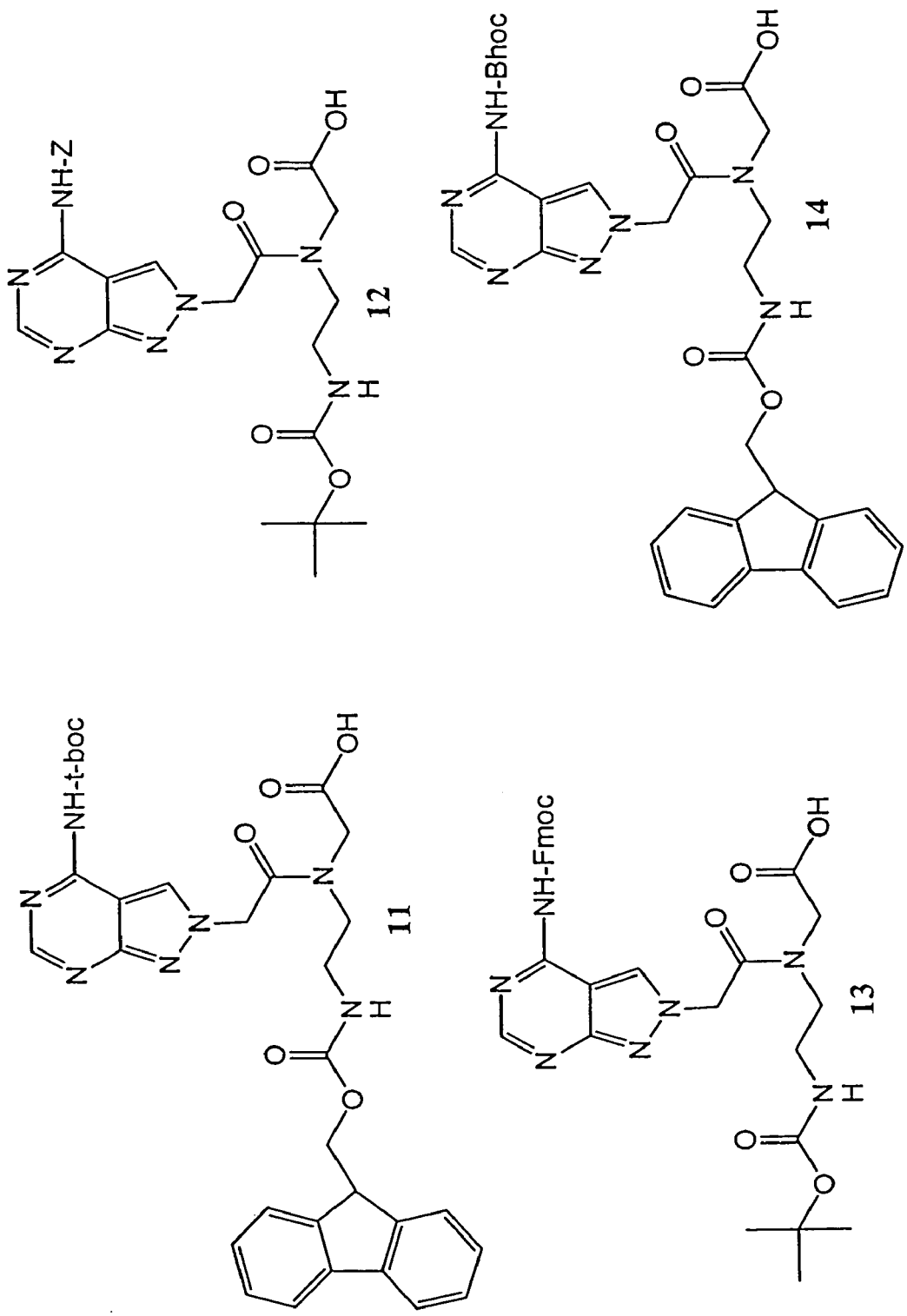
Figure 7B:
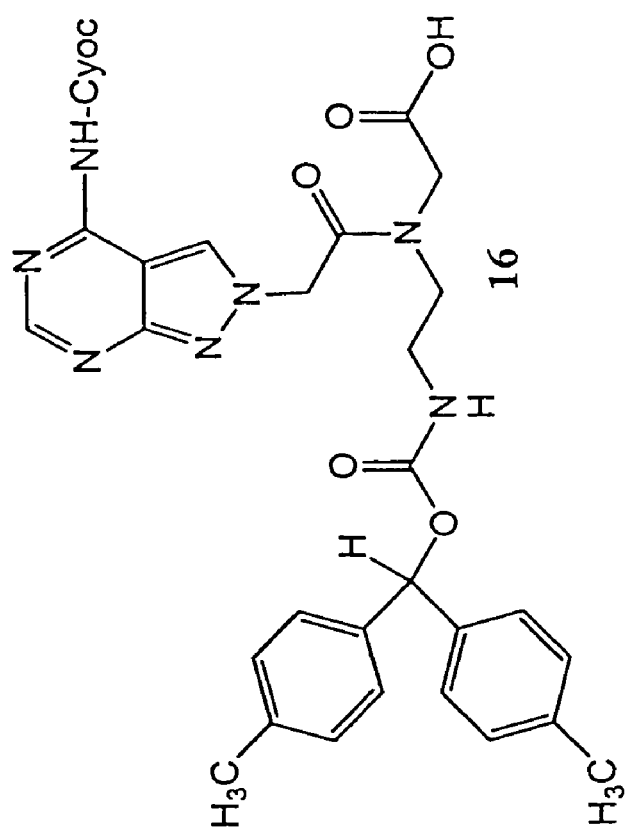
Figure 7B:
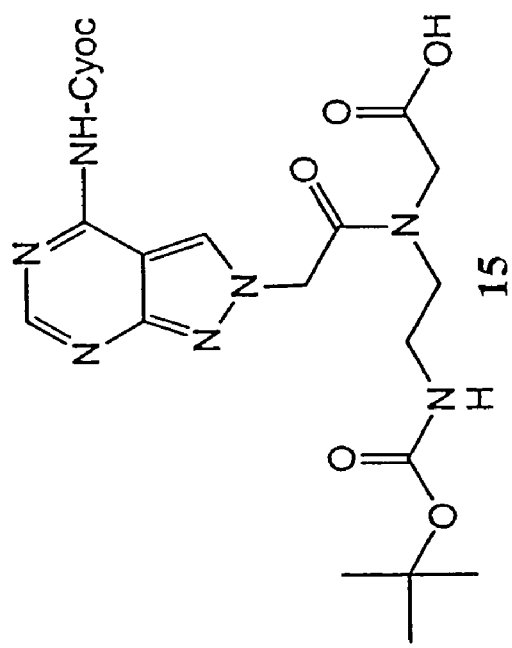

FIGS. 7A and 7B illustrate various PNA synthons comprising a protected N8-alkylated 8-aza-7-deazaadenine nucleobase.

Figure 8A:
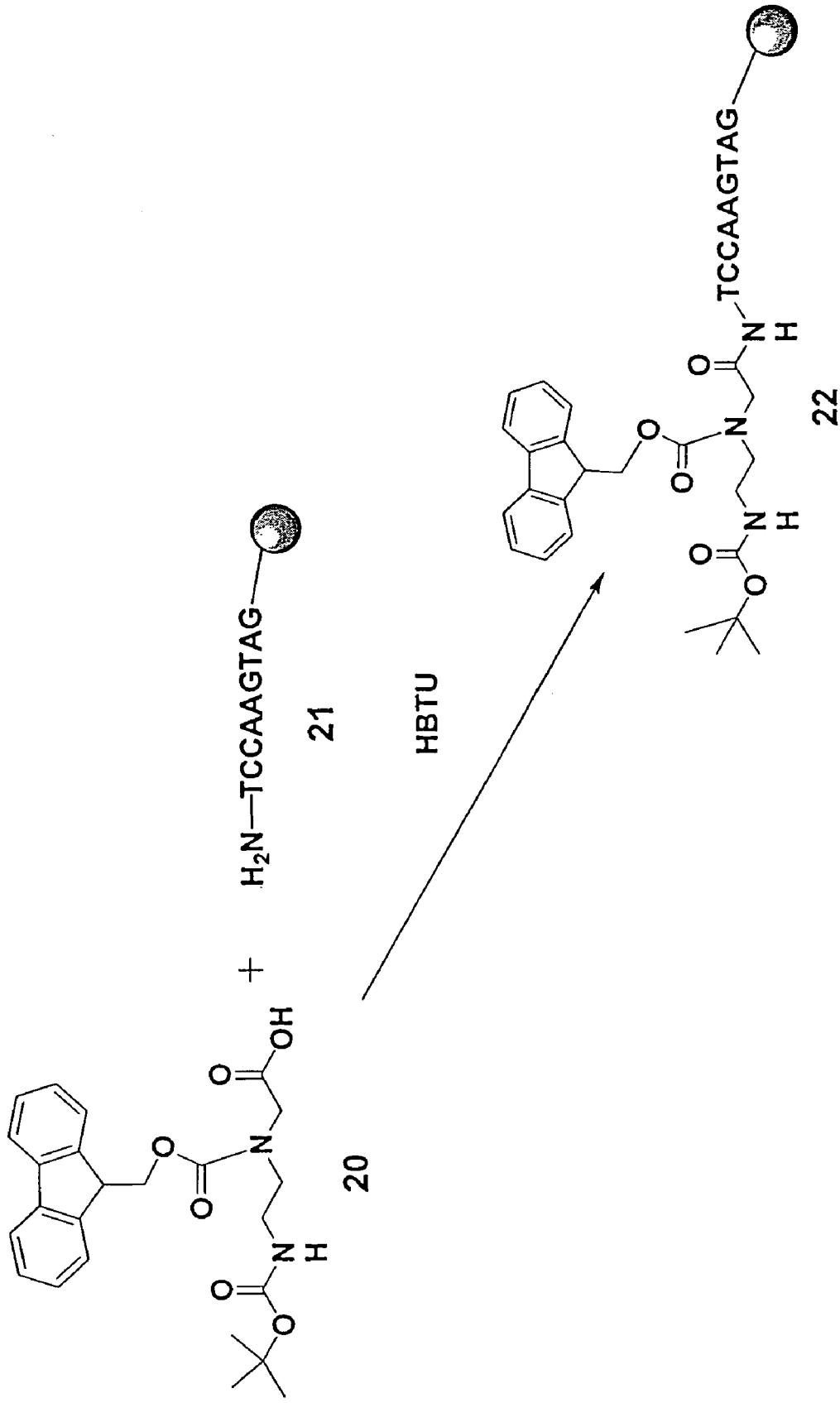
Figure 8B:
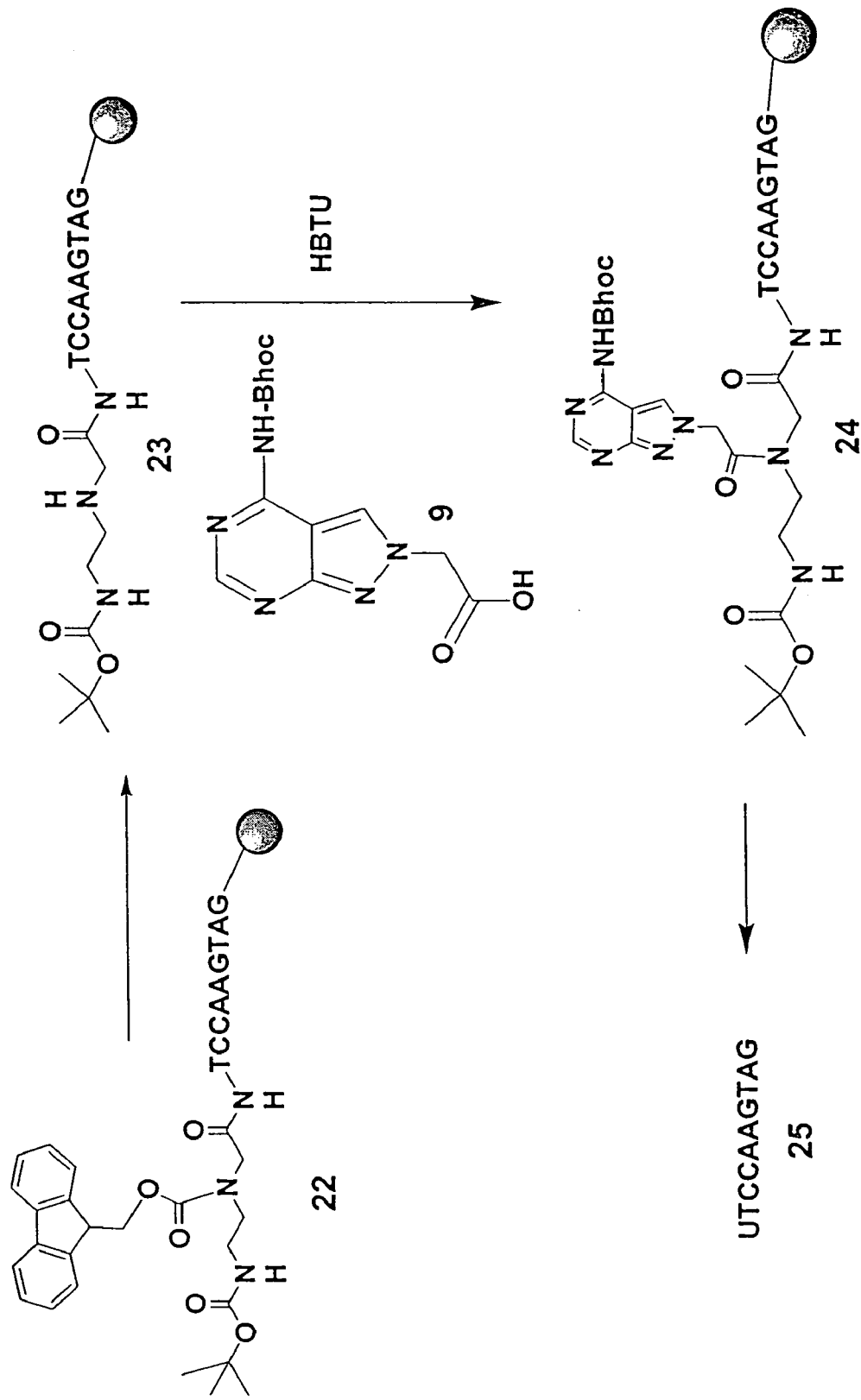

FIGS. 8A and 8B illustrate the coupling of a partially protected N8-alkylated 8-aza-7-deazaadenine nucleobase directly to the backbone of a support bound PNA oligomer.

All literature and similar materials cited in this application, including but not limited to, patents, patent applications, articles, books, treatises, and internet web pages, regardless of the format of such literature and similar materials, are expressly incorporated by reference herein in their entirety for any and all purposes.

4. DEFINITIONS

Figure 1A:
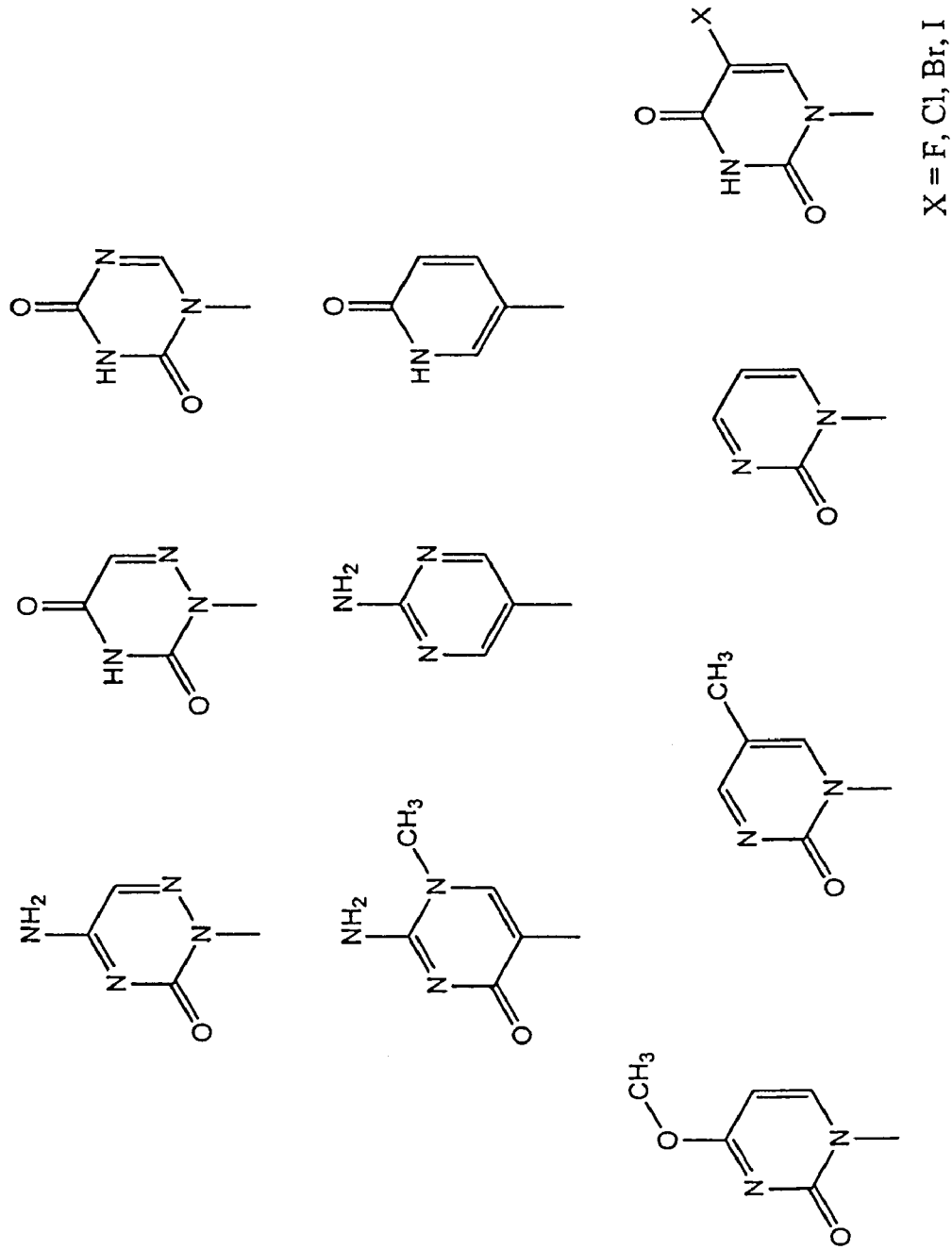
FIGS. 1A and 1B are illustrations of some nucleobases that can be incorporated into nucleic acids, PNA oligomers and PNA/DNA Chimeras.
Figure 1B:
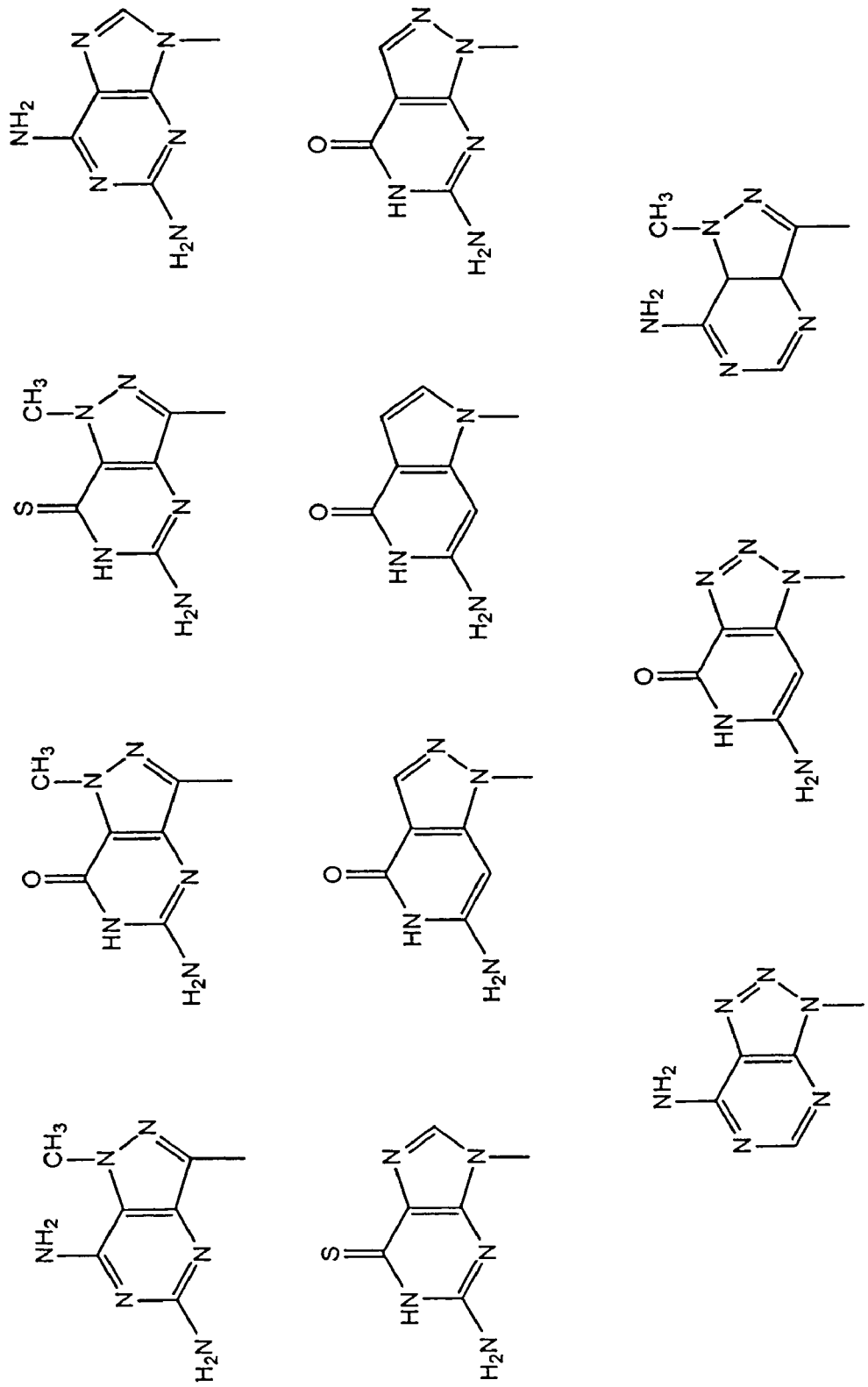

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall control.

a. As used herein, "nucleobase" refers to those naturally occurring and those non-naturally occurring heterocyclic moieties commonly known to those who utilize nucleic acid technology or utilize peptide nucleic acid technology to thereby generate polynucleobase strands that can sequence specifically bind to nucleic acids and other polynucleobase strands. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil, 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(8-aza-7-deazaadenine). Other non-limiting examples of suitable nucleobase include those nucleobases illustrated in FIGS. 1A and 1B (also see FIGS. 2A and 2B of U.S. Pat. No. 6,357,163).

b. As used herein, "nucleobase sequence" refers to any segment, or aggregate of two or more segments (i.e. linked polymer), of a polynucleobase strand. Non-limiting examples of suitable polynucleobase strands include oligodeoxynucleotides (e.g. DNA), oligoribonucleotides (e.g. RNA), peptide nucleic acids (PNA), PNA/DNA Chimeras, nucleic acid analogs and/or nucleic acid mimics.

c. As used herein, the phrase "nucleobase containing subunit" refers to a subunit of a polynucleobase strand that comprises a nucleobase. For oligonucleotides, the nucleobase containing subunit is a nucleotide. With reference to oligonucleotides, those of skill in the art will appreciate the form of a subunit associated with other species of polynucleobase strands.

d. As used herein, "polynucleobase strand" refers to a complete single polymer strand comprising nucleobase-containing subunits.

e. As used herein, "nucleic acid" refers to a polynucleobase strand having a backbone formed from nucleotides, or analogs thereof. Preferred nucleic acids are DNA, RNA, L-DNA, locked nucleic acids (LNA). For the avoidance of any doubt, PNA is a nucleic acid mimic and not a nucleic acid or nucleic acid analog. PNA is not a nucleic acid since it is not formed from nucleotides.

f. As used herein, "peptide nucleic acid" or "PNA" refers to any polynucleobase strand or segment of a polynucleobase strand comprising two or more PNA subunits, including, but not limited to, any polynucleobase strand or segment of a polynucleobase strand referred to or claimed as a peptide nucleic acid in U.S. Pat. Nos. 5,539,082, 5,527,675, 5,623, 049, 5,714,331, 5,718,262, 5,736,336, 5,773,571, 5,766,855, 5,786,461, 5,837,459, 5,891,625, 5,972,610, 5,986,053, 6,107,470 and 6,357,163.

The term "peptide nucleic acid" or "PNA" shall also apply to any polynucleobase strand or segment of a polynucleobase strand comprising two or more subunits of those nucleic acid mimics described in the following publications: Lagriffoul et al., *Bioorganic & Medicinal Chemistry Letters*, 4: 1081-1082 (1994); Petersen et al., *Bioorganic & Medicinal Chemistry Letters*, 6: 793-796 (1996); Diderichsen et al., *Tett. Lett.* 37: 475-478 (1996); Fujii et al., *Bioorg. Med. Chem. Lett.* 7: 637-627 (1997); Jordan et al., *Bioorg. Med. Chem. Lett.* 7: 687-690 (1997); Krotz et al., *Tett. Lett.* 36: 6941-6944 (1995); Lagriffoul et al., *Bioorg. Med. Chem. Lett.* 4: 1081-1082 (1994); Diederichsen, U., *Bioorganic & Medicinal Chemistry Letters*, 7: 1743-1746 (1997); Lowe et al., *J. Chem. Soc. Perkin Trans.* 1, (1997) 1: 539-546; Lowe et al., *J. Chem. Soc. Perkin Trans.* 11: 547-554 (1997); Lowe et al., *J. Chem. Soc. Perkin Trans.* 11:5 55-560 (1997); Howarth et al., *J. Org. Chem.* 62: 5441-5450 (1997); Altmann, K-H et al., *Bioorganic & Medicinal Chemistry Letters*, 7: 1119-1122 (1997); Diederichsen, U., *Bioorganic & Med. Chem. Lett.*, 8: 165-168 (1998); Diederichsen et al., *Angew. Chem. Int. Ed.*, 37:302-305 (1998); Cantin et al., *Tett. Lett.*, 38:4211-4214 (1997); Ciapetti et al., *Tetrahedron*, 53: 1167-1176 (1997); Lagriffoule et al., *Chem. Eur. J.*, 3: 912-919 (1997); Kumar et al., *Organic Letters* 3(9): 1269-1272 (2001); and the Peptide-Based Nucleic Acid Mimics (PENAMs) of Shah et al. as disclosed in WO96/04000.

In some embodiments, a "peptide nucleic acid" or "PNA" is a polynucleobase strand or segment of a polynucleobase strand comprising two or more covalently linked subunits of the formula:

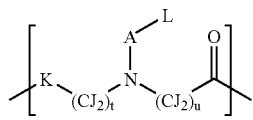

wherein, each J is the same or different and is selected from the group consisting of: H, R', OR', SR', NHR', NR'$_2$, F, Cl, Br and I. Each K is the same or different and is selected from the group consisting of: O, S, NH and NR'. Each R' is the same or different and is an alkyl group, an alkenyl group, an alkynyl group, an aryl group, a heteroalkyl, an heteroalkenyl group, a heteralkynyl group, a heteroaryl group, an arylalkyl group, a heteroarylalkyl group. For example, R' can be methyl, ethyl, n-propyl, isopropyl, n-butyl, sec-butyl, tert-butyl, iso-butyl, n-pentyl, n-hexyl, methoxy, ethoxy, benzyl, phenyl, vinyl or allyl.

Each A is selected from the group consisting of: a single bond, a group of the formula; —(CJ$_2$)$_s$— and a group of the formula; —(CJ$_2$)$_n$C(O)—, wherein, J is defined above and each s is a integer from one to five. Each t is 1 or 2 and each u is 1 or 2. Each L is the same or different and is independently selected from: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine), N8-(8-aza-7-deazaadenine), other naturally occurring nucleobase analogs and other non-naturally occurring nucleobases (e.g. FIGS. 1A and 1B).

In some embodiments, a PNA subunit can be a naturally occurring or non-naturally occurring nucleobase attached to the N-α-glycyl nitrogen of the N-[2-(aminoethyl)]glycine backbone through a methylene carbonyl linkage; this currently being the most commonly used form of a peptide nucleic acid subunit.

g. As used herein, "sequence specifically" refers to hybridization by base pairing through hydrogen bonding. Non-limiting examples of standard base pairing include adenine base pairing with thymine or uracil and guanine base pairing with cytosine. Other non-limiting examples of base-pairing motifs include, but are not limited to: adenine base pairing with any of: 5-propynyl-uracil, 2-thio-5-propynyl-uracil, 2-thiouracil or 2-thiothymine; guanine base pairing with any of: 5-methylcytosine or pseudoisocytosine; cytosine base pairing with any of: hypoxanthine, N9-(7-deaza-guanine) or N9-(7-deaza-8-aza-guanine); thymine or uracil base pairing with any of: 2-aminopurine, N9-(2-amino-6-chloropurine) or N9-(2,6-diaminopurine); and N8-(8-aza-7-deazaadenine), being a universal base, base pairing with any other nucleobase, such as for example any of: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine).

h. As used herein, the term "chimera" or "chimeric oligomer" refers to a polynucleobase strand comprising two or more linked subunits that are selected from different classes of subunits. For example, a PNA/DNA chimera can comprise at least one PNA subunit linked to at least one 2'-deoxyribonucleic acid subunit (For exemplary methods and compositions related to PNA/DNA chimera preparation See: U.S. Pat. No. 6,063,569).

i. As used herein, the term "linked polymer" refers to a polynucleobase strand comprising two or more polymer segments that are linked by a linker. The polymer segments that can be linked to form the linked polymer can be selected from the group consisting of an oligodeoxynucleotide, an oligoribonucleotide, a peptide, a polyamide, a peptide nucleic acid (PNA) and a PNA/DNA Chimera.

j. As used herein, the term "alkyl" refers to a straight chained or branched C$_1$-C$_{20}$ hydrocarbon or a cyclic C$_3$-C$_{20}$ hydrocarbon (i.e. a cycloalkyl group) that is completely saturated. When used herein, the term "alkyl" refers to a group that may be substituted or unsubstituted. When used herein, "alkyl" also refers to an alkyl group wherein one or more of the carbon atoms of a substituted or unsubstituted methylene group may be replaced by a silicon atom (Si). In some embodiments, alkyl groups can be a straight chained or branched C$_1$-C$_6$ hydrocarbons or cyclic C$_3$-C$_6$ hydrocarbons that are completely saturated.

k. As used herein, the term "alkylene" refers to a straight or branched alkyl chain or a cyclic alkyl group that has at least two points of attachment to at least two moieties (e.g., —{CH$_2$}— (methylene), —{CH$_2$CH$_2$}—, (ethylene),

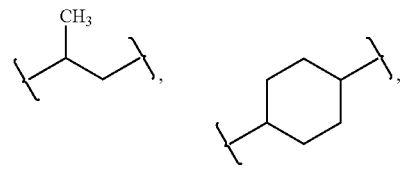

etc., wherein the brackets indicate the points of attachment). When used herein the term "alkylene" refers to a group that may be substituted or unsubstituted. In some embodiments, an alkylene group can be a $C_1$-$C_6$ hydrocarbon.

l. As used herein, the term "alkenyl" refers to straight chained or branched $C_2$-$C_{20}$ hydrocarbons or cyclic $C_3$-$C_{20}$ hydrocarbons that have one or more double bonds. When used herein, the term "alkenyl" refers to a group that can be substituted or unsubstituted. For the purposes of this specification, "alkenyl" can also refer to an alkenyl group wherein one or more of the carbon atoms of a substituted or unsubstituted methylene group has been replaced by a silicon atom (Si). In some embodiments, alkenyl groups can be straight chained or branched $C_2$-$C_6$ hydrocarbons or cyclic $C_3$-$C_6$ hydrocarbons that have one or more double bonds.

m. As used herein, the term "alkynyl" refers to straight chained or branched $C_2$-$C_{20}$ hydrocarbons or cyclic $C_3$-$C_{20}$ hydrocarbons that have one or more triple bonds. When used herein, the term "alkynyl" refers to a group that can be substituted or unsubstituted. For the purposes of this specification, "alkynyl" will also refer to an alkynyl group wherein one or more of the carbon atoms of a substituted or unsubstituted methylene group has been replaced by a silicon atom (Si). In some embodiments, alkynyl groups can be straight chained or branched $C_2$-$C_6$ hydrocarbons or cyclic $C_3$-$C_6$ hydrocarbons that have one or more triple bonds.

n. As used herein, the term "heteroalkyl" refers to an alkyl group in which one or more methylene groups in the alkyl chain is replaced by a heteroatom such as —O—, —S—, —$SO_2$— or —NR"—, wherein R" can be a hydrogen, alkyl, alkenyl, alkynyl, aryl or arylalkyl. When used herein, the term "heteroalkyl" refers to a group that can be substituted or unsubstituted.

o. As used herein, the term "heteroalkenyl" refers to an alkenyl group in which one or more methylene groups is replaced by a heteroatom such as —O—, —S—, —$SO_2$— or —NR"—, wherein R" is previously defined. When used herein, the term "heteroalkenyl" refers to a group that can be substituted or unsubstituted.

p. As used herein, the term "heteroalkynyl" refers to an alkynyl group in which one or more methylene groups is replaced by a heteroatom such as —O—, —S—, —$SO_2$— or —NR"—, wherein R" is previously defined. When used herein, the term "heteroalkenyl" refers to a group that can be substituted or unsubstituted.

q. As used herein, the term "heterocycloalkyl" refers to a non-aromatic ring that comprises one or more oxygen, nitrogen or sulfur atoms (e.g., morpholine, piperidine, piperazine, pyrrolidine, and thiomorpholine). As used herein, the term "heterocycloalkyl" refers to a group that may be substituted or unsubstituted.

r. As used herein, the term "aryl", either alone or as part of another moiety (e.g., arylalkyl, etc.), refers to carbocyclic aromatic groups such as phenyl. Aryl groups also include fused polycyclic aromatic ring systems in which a carbocyclic aromatic ring is fused to another carbocyclic aromatic ring (e.g., 1-naphthyl, 2-naphthyl, 1-anthracyl, 2-anthracyl, etc.) or in which a carbocylic aromatic ring is fused to one or more carbocyclic non-aromatic rings (e.g., tetrahydronaphthylene, indan, etc.). As used herein, the term "aryl" refers to a group that may be substituted or unsubstituted.

s. As used herein, the term "heteroaryl" refers to an aromatic heterocycle that comprises 1, 2, 3 or 4 heteroatoms independently selected from nitrogen, sulfur and oxygen. As used herein, the term "heteroaryl" refers to a group that may be substituted or unsubstituted. A heteroaryl may be fused to one or two rings, such as a cycloalkyl, a heterocycloalkyl, an aryl, or a heteroaryl. The point of attachment of a heteroaryl to a molecule may be on the heteroaryl, cycloalkyl, heterocycloalkyl or aryl ring, and the heteroaryl group may be attached through carbon or a heteroatom. Heteroaryl groups may be substituted or unsubstituted. Examples of heteroaryl groups include imidazolyl, furyl, pyrrolyl, thienyl, oxazolyl, thiazolyl, isoxazolyl, isothiazolyl, thiadiazolyl, oxadiazolyl, pyridinyl, pyrimidyl, pyrazinyl, pyridazinyl, quinolyl, isoquinolinyl, indazolyl, benzoxazolyl, benzisooxazolyl, benzofuryl, benzothiazolyl, indolizinyl, imidazopyridinyl, pyrazolyl, triazolyl, isothiazolyl, oxazolyl, tetrazolyl, benzimidazolyl, benzothiazolyl, benzoisothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidyl, pyrazolo[3,4]pyrimidyl or benzo(b)thienyl, each of which can be optionally substituted.

t. As used herein, the term "arylalkyl" refers to an aryl group that is attached to another moiety via an alkylene linker. As used herein, the term "arylalkyl" refers to a group that may be substituted or unsubstituted.

u. As used herein, the term "heteroarylalkyl" refers to a heteroaryl group that is attached to another moiety (e.g. an alkyl or heteroalkyl group) via an alkylene linker. As used herein, the term "heteroarylalkyl" refers to a group that may be substituted or unsubstituted.

Suitable substituents for any alkyl, an alkylene, an alkenyl, an alkynyl, a heteroalkyl, a heteroalkenyl, a heteroalkynyl, an aryl, a heteroaryl, an arylalkyl, or a heteroarylalkyl group includes any substituent that is stable under the reaction conditions used in embodiments of this invention. Non limiting examples of suitable substituents include: an alkyl (e.g., methyl, ethyl, n-propyl, isopropyl, n-butyl, isobutyl, sec butyl, t-butyl, cyclohexyl etc.) group, a haloalkyl (e.g., trifluoromethyl, 2,2,2-trifluoroethyl-) group, an alkoxy (e.g., methoxy, ethoxy, etc.) group, an aryl (e.g., phenyl) group, an arylalkyl (e.g., benzyl) group, a nitro group, a cyano group, a quaternized nitrogen atom, or a halo (e.g., fluorine, chlorine, bromine and iodine) group.

In addition, any saturated portion of an alkyl, alkenyl, alkynyl, heteroalkyl, heteroalkenyl, heteroalkynyl, arylalkyl or heteroarylalkyl group, may also be substituted with =O, =S, =N—R", wherein R" is previously defined.

When a heteroalkyl, heteroalkenyl, heteroalkynyl, or heteroarylalky group contains a nitrogen atom, it may be substituted or unsubstituted. When a nitrogen atom in the aromatic ring of a heteroaryl group has a substituent, the nitrogen may be a quaternary nitrogen.

v. As used herein, "amino acid" refers to a group represented by R'"—NH—CH(R"")—C(O)—R'", wherein each R'" is independently hydrogen, an aliphatic group, a substituted aliphatic group, an aromatic group, another amino acid, a peptide or a substituted aromatic group. A "naturally-occurring amino acid" is an amino acid found in nature. Examples include alanine, valine, leucine, isoleucine, aspartic acid, glutamic acid, serine, threonine, glutamine, asparagine, arginine, lysine, ornithine, proline, hydroxyproline, phenylalanine, tyrosine, tryptophan, cysteine, methionine and histidine. In some embodiments, R"" can be hydrogen or a side-chain of a naturally-occurring amino acid. Examples of naturally occurring amino acid side-chains include methyl (alanine), isopropyl (valine), sec-butyl (isoleucine), —$CH_2CH$(—$CH_3$)$_2$ (leucine), benzyl (phenylalanine), p-hydroxybenzyl (tyrosine), —$CH_2$—OH (serine), —$CHOHCH_3$ (threonine), —CH$_2$-3-indoyl (tryptophan), —CH$_2$COOH (aspartic acid), —CH$_2$CH$_2$COOH (glutamic acid), —CH$_2$C(O)NH$_2$ (asparagine), —CH$_2$CH$_2$C(O)NH$_2$ (glutamine), —CH$_2$SH, (cysteine), —CH$_2$CH$_2$SCH$_3$ (methionine), —(CH$_2$)$_4$NH$_2$ (lysine), —(CH$_2$)$_3$NH$_2$ (ornithine), —{(CH$_2$)$_2$}$_4$NHC(=NH)NH$_2$ (arginine) and —CH$_2$-3-imidazoyl (histidine).

Side-chains of amino acids comprising a heteroatom-containing functional group, e.g., an alcohol (serine, tyrosine, hydroxyproline and threonine), an amine (lysine, ornithine, histidine and arginine), may require a protecting group to facilitate reactions discussed herein. When the heteroatom-containing functional group is modified to include a protecting group, the side-chain is referred to as the "protected side-chain" of an amino acid. Protecting groups are commonly used in peptide synthesis and these are known to, and often used by, the ordinary practitioner. For example, many suitable protecting groups, and methods for the preparation of protected amino acids, can be found in Green et al., Protecting Groups In Organic Synthesis, Third Edition, John Wiley & Sons, Inc. New York, 1999.

w. As used herein, the term "salt form" includes a salt of a compound or a mixture of salts of a compound. In addition, zwitterionic forms of a compound are also included in the term "salt form." Salts of compounds having an amine, or other basic group can be obtained, for example, by reacting with a suitable organic or inorganic acid, such as hydrogen chloride, hydrogen bromide, acetic acid, perchloric acid and the like. Compounds with a quaternary ammonium group may also contain a counteranion such as chloride, bromide, iodide, acetate, perchlorate and the like. Salts of compounds having a carboxylic acid, or other acidic functional group, can be prepared by reacting the compound with a suitable base, for example, a hydroxide base. Accordingly, salts of acidic functional groups may have a countercation, such as sodium, potassium, magnesium, calcium, etc.

5. DESCRIPTION

I. General:

It is to be understood that the discussion set forth below in this "General" section can pertain to some, or to all, of the various embodiments of the invention described herein.

PNA Synthesis:

Methods for the chemical assembly of PNAs are known (See for example: U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470). As a general reference for PNA synthesis methodology please see: Nielsen et al., *Peptide Nucleic Acids; Protocols and Applications*, Horizon Scientific Press, Norfolk England (1999).

Chemicals and instrumentation for the support bound automated chemical assembly of peptide nucleic acids are available. Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus that can be condensed with the next synthon to be added to the growing polymer. Because standard peptide chemistry is utilized, natural and non-natural amino acids can be routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide. The orientation of hybridization is not a limitation however, since PNA oligomers are also known to bind in parallel orientation to both nucleic acids and other PNA oligomers.

PNA Labeling:

Non-limiting methods for labeling PNA oligomers are described in U.S. Pat. Nos. 6,110,676, 6,355,421, 6,361,942 and 6,485,901 or are otherwise known in the art of PNA synthesis. Other non-limiting examples for labeling PNA oligomers are also discussed in Nielsen et al., *Peptide Nucleic Acids; Protocols and Applications*, Horizon Scientific Press, Norfolk England (1999). PNA oligomers and oligonucleotides can also be labeled with proteins (e.g. enzymes) and peptides as described in U.S. Pat. No. 6,197,513. Thus, a variety of labeled PNA oligomers can be prepared or purchased from commercial vendors.

Nucleic Acid Synthesis and Modification

Nucleic acid oligomer (oligonucleotide and oligoribonucleotide) synthesis has become routine. For a detailed description of nucleic acid synthesis please see Gait, M. J., *Oligonucleotide Synthesis: a Practical Approach*. IRL Press, Oxford England. Those of ordinary skill in the art will recognize that both labeled and unlabeled oligonucleotides (DNA, RNA and synthetic analogues thereof) are readily available. They can be synthesized using commercially available instrumentation and reagents or they can be purchased from commercial vendors of custom manufactured oligonucleotides.

PNA/DNA Chimera Synthesis and Modification:

PNA/DNA Chimeras are a combination of nucleic acid and peptide nucleic acid subunits. A suitable reference for the synthesis, labeling and modification of PNA/DNA Chimeras can be found in U.S. Pat. No. 6,063,569. Moreover, the methods described above for PNA synthesis and labeling often can be used to modify the PNA portion of a PNA/DNA Chimera. Additionally, known methods for the synthesis and labeling of nucleic acids can often be used to modify the nucleic acid portion of a PNA/DNA Chimera. Hence, the synthesis, labeling and modification of PNA/DNA Chimeras can utilize methods known to those of skill in the art as well as those described, or made reference to, above.

Labels:

PNA oligomers and PNA/DNA Chimeras can comprise a label. Non-limiting examples of detectable moieties (labels) that can be used to label polynucleobase strands (e.g. PNA oligomers) include a dextran conjugate, a branched nucleic acid detection system, a chromophore, a fluorophore, a spin label, a radioisotope, an enzyme, a hapten, an acridinium ester or a chemiluminescent compound. Other suitable labeling reagents and preferred methods of attachment would be recognized by those of ordinary skill in the art of PNA, peptide or nucleic acid synthesis.

Non-limiting examples of haptens include 5(6)-carboxyfluorescein, 2,4-dinitrophenyl, digoxigenin, and biotin.

Non-limiting examples of fluorochromes (fluorophores) include 5(6)-carboxyfluorescein (Flu), 6-((7-amino-4-methylcoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dye series (Molecular Probes, Eugene, Oreg.).

Non-limiting examples of enzymes include polymerases (e.g. Taq polymerase, Klenow DNA polymerase, T7 DNA polymerase, Sequenase, DNA polymerase 1 and phi29 polymerase), alkaline phosphatase (AP), horseradish peroxidase (HRP), soy bean peroxidase (SBP)), ribonuclease and protease.

Spacer/Linker Moieties:

PNA oligomers and PNA/DNA Chimeras can comprise a spacer and/or linker moiety. Generally, spacers are used to minimize the adverse effects that bulky labeling reagents might have on hybridization properties of probes. Linkers typically induce flexibility and randomness into the polynucleobase strand or otherwise link two or more nucleobase sequences of a polynucleobase strand. Preferred spacer/linker moieties for the polynucleobase strands described herein can comprise one or more aminoalkyl carboxylic acids (e.g. aminocaproic acid), the side chain of an amino acid (e.g. the side chain of lysine or ornithine), natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties can also incidentally or intentionally be constructed to improve the water solubility of the polynucleobase strand (For example see: Gildea et al., *Tett. Lett.* 39: 7255-7258 (1998) and U.S. Pat. Nos. 6,326,479 and 6,770,442).

For example, a spacer/linker moiety can comprise one or more linked compounds having the formula: —Q—(O$_m$—(CM$_2$)$_n$)$_o$—T—. The group Q can be selected from the group consisting of: a single bond, —(CM$_2$)$_p$—, —C(O)(CM$_2$)$_p$—, —C(S)(CM$_2$)$_p$— and —S(O$_2$)(CM$_2$)$_p$—. The group T can have the formula NH, NR'''', S, —SO$_2$— or O. Each M can be independently H, R'''', —OR'''', F, Cl, Br or I; wherein, each R'''' can be independently selected from the group consisting of: —CV$_3$, —CV$_2$CV$_3$, —CV$_2$CV$_2$CV$_3$, —CV$_2$CV(CV$_3$)$_2$ and —C(CV$_3$)$_3$, wherein each V can be independently hydrogen (H), fluorine (F), chlorine (Cl), bromine (Br) or iodine (I). Each m can be independently 0 or 1. Each n, o and p can be independently integers from 0 to 10. In some embodiments, each n, o and p can be independently integers from 0 to 3.

II. Various Embodiments of the Invention a. Methods:

i) Alkylation

The methods of this invention relate generally to the production of compositions comprising 8-aza-7-deazaadenine, including intermediates for the production of said compositions. These methods are useful in the production of PNA monomers and PNA oligomers comprising 8-aza-7-deazaadenine. In said PNA oligomers, 8-aza-7-deazaadenine can function as a universal base. By universal base we mean that 8-aza-7-deazaadenine can form specific hydrogen bonds to the nucleobases adenine, thymine, guanine or cytosine in other polynucleobase strands. Accordingly, PNA oligomers comprising the nucleobase 8-aza-7-deazaadenine can sequence specifically hybridize to complementary polynucleobase strands wherein any of adenine, thymine, guanine or cytosine can be opposite to the 8-aza-7-deazaadenine in the complementary polynucleobase strand.

Accordingly, in some embodiments, this invention pertains to methods for the alkylation of a substituted or unsubstituted 3-aminopyrazole-4-carbonitrile compound. By reference to a substituted 3-aminopyrazole-4-carbonitrile, we refer to the substitution of the hydrogen atom at carbon 5 of the pyrazole ring. The substituent substituted for the hydrogen atom of carbon 5 can be an alkyl group, an alkenyl group, an alkynyl group, a heteroalkyl group, a heteroalkenyl group, a heteroalkynyl group, an aryl group, a heteroaryl group, an arylalkyl group or a heteroarylalkyl group, provided that the substituent does not comprise one or more groups that is reactive during the alkylation reaction. Potentially reactive groups can be protected with a protecting group as described in Green et al., Protecting Groups In Organic Synthesis, Third Edition, John Wiley & Sons, Inc. New York, 1999 and then deprotected as appropriate.

Figure 2:
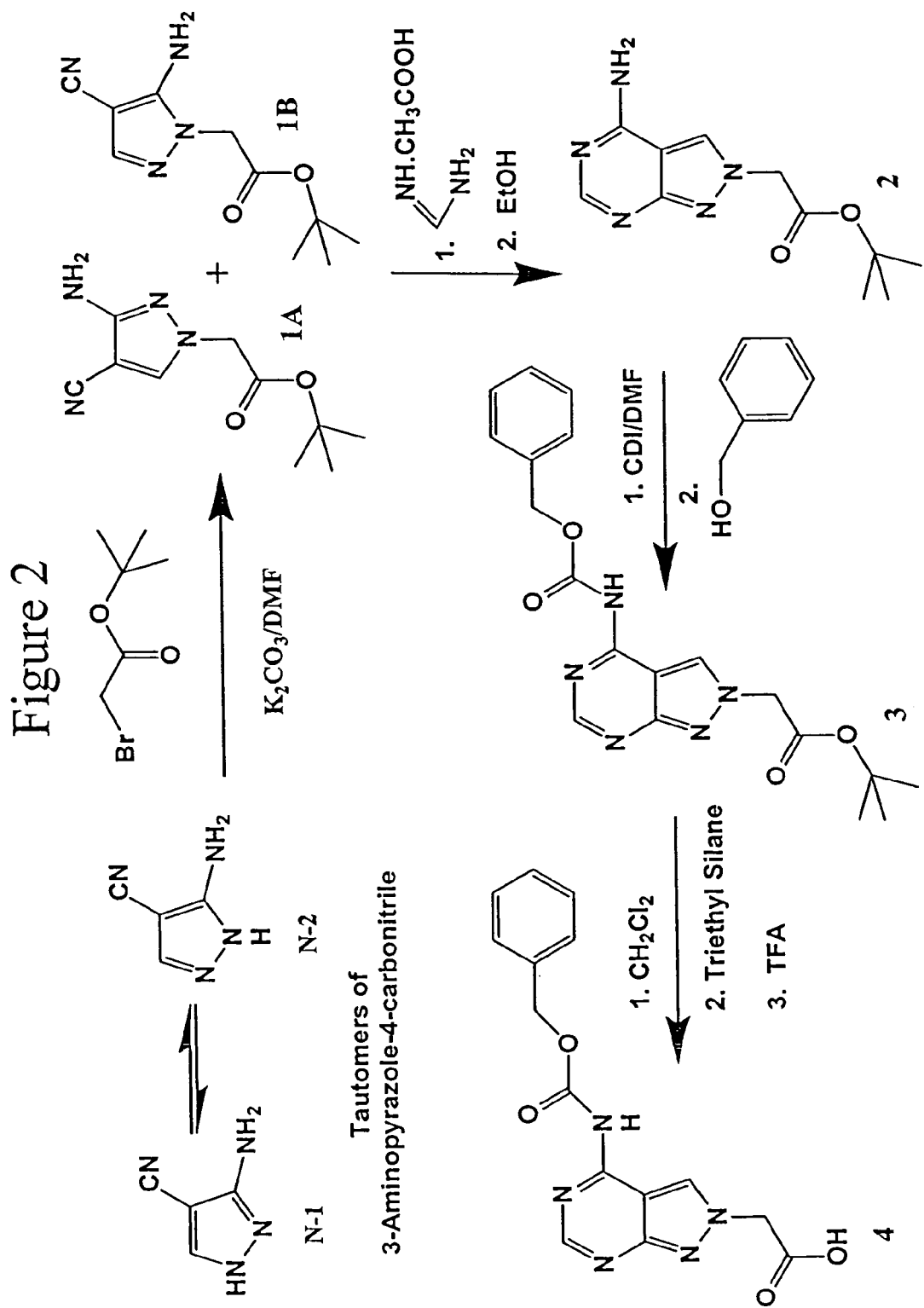
FIG. 2 is an illustration of a synthetic route to a Z-protected N8-alkylated 8-aza-7-deazaadenine compound.
Figure 3:
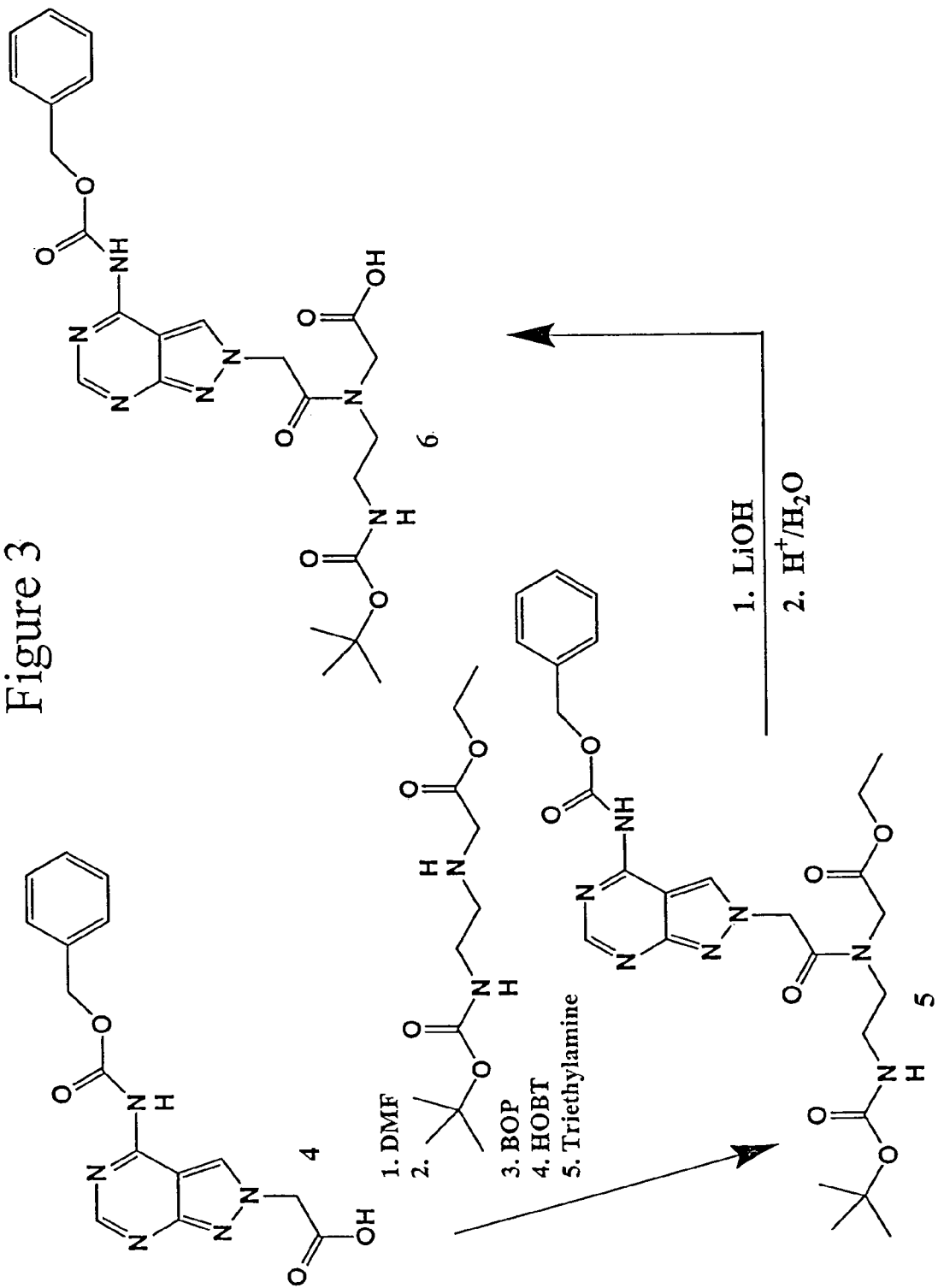
FIG. 3 is an illustration of a synthetic route to a t-boc PNA monomer comprising Z-protected N8-alkylated 8-aza-7-deazaadenine.
Figure 4:
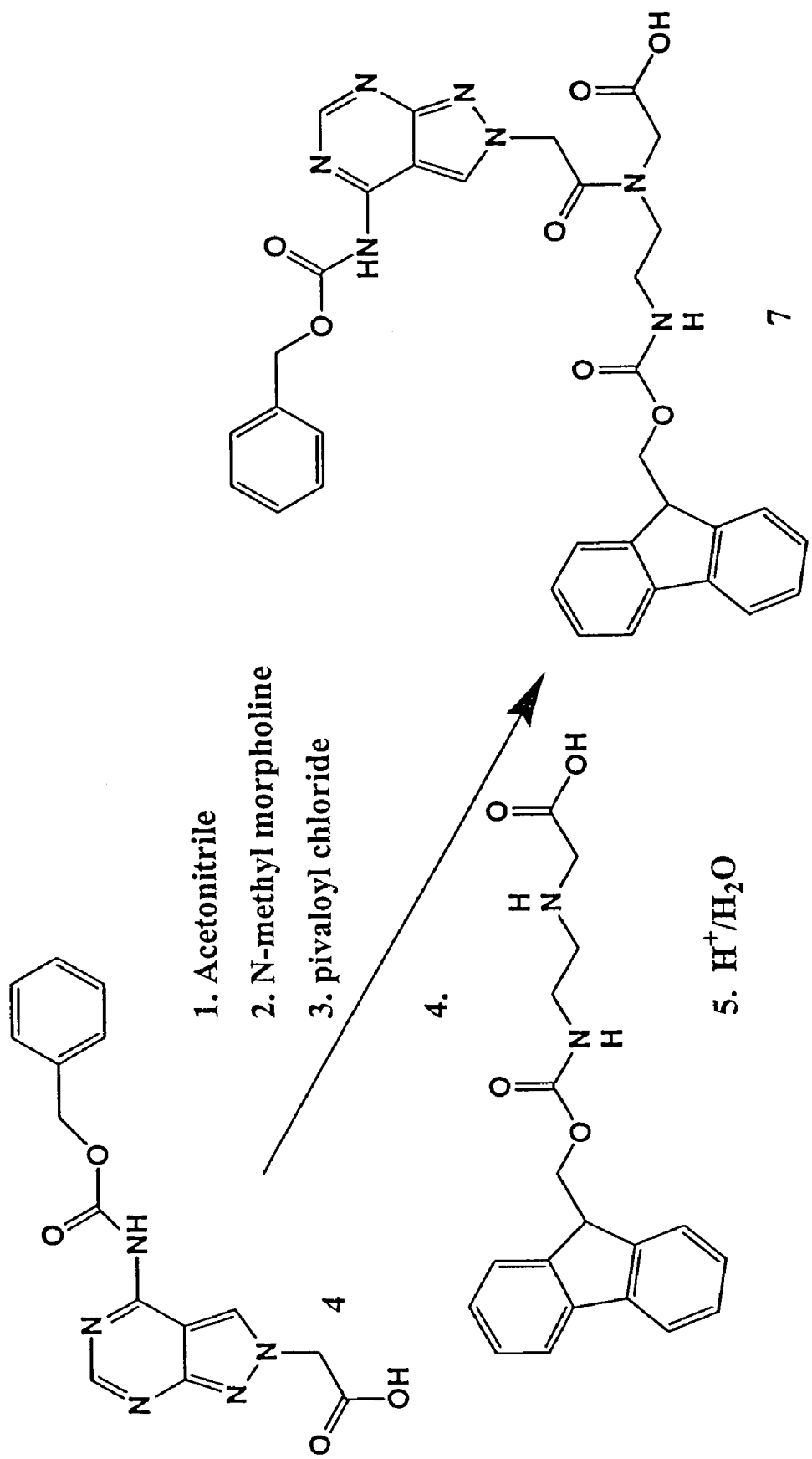
FIG. 4 illustrates a synthetic route to an Fmoc/Z PNA monomer comprising a protected N8-alkylated 8-aza-7-deazaadenine nucleobase.

With reference to FIG. 2, two tautomers of 3-aminopyrazole-4-carbonitrile are known to exist. These are known as the N-1 and N-2 tautomer based upon the numbering of the pyrazole ring. Alkylation can proceed at one of the two ring nitrogen atoms, but in some embodiments can occur at either of the nitrogen atoms without preference. Because of the presence of the two tautomeric forms, alkylation of 3-aminopyrazole-4-carbonitrile results in the formation of two different products (i.e. the N-1 or N-2 alkylated forms identified in the FIG. 2 as compounds 1A and 1B, respectively). The N-1 alkylated 3-aminopyrazole-4-carbonitrile can be used for the preparation of an N-8 alkylated form of 8-aza-7-deazaadenine. Although Applicants have determined that the specific compositions shown in FIG. 2 (i.e. 1A & 1B) can be separated by crystallization techniques, chromatography or other separations techniques can be applied to effect the separation of other alkylated compounds that do not separate by crystallization. Suitable separations techniques will be known to the ordinary practitioner of organic chemistry.

Many haloacetic acid derivatives as well as various esters of haloacetic acid are commercially available. Alkylating reagents useful for alkylating the substituted or unsubstituted 3-aminopyrazole-4-carbonitrile can be a halo acetate compound of the formula:

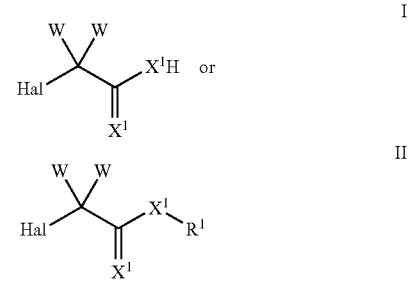

wherein each W can be independently hydrogen, an alkyl group, an alkenyl group, an alkynyl group, a heteroalkyl group, a heteroalkenyl group, a heteroalkynyl group, an aryl group, a heteroaryl group, an arylalkyl group or a heteroarylalkyl group. The group R$^1$ can be an alkyl group, an alkenyl group, an alkynyl group, a heteroalkyl group, a heteroalkenyl group, a heteroalkynyl group, an aryl group, a heteroaryl group, an arylalkyl group or a heteroarylalkyl group. Hal can be chlorine (Cl), bromine (Br) or iodine (I). Each X$^1$ can independently be O or S. Each X$^1$ can be O.

Alkylation of the substituted or unsubstituted 3-aminopyrazole-4-carbonitrile can be performed under basic conditions in a polar aprotic organic solvent using a haloacetic acid or an ester of a halo acetic acid. The conditions used for alkylating the substituted or unsubstituted 3-aminopyrazole-4-carbonitrile can be substantially similar to the conditions used for alkylating nucleobases as applied to the production of PNA monomers (See: U.S. Pat. Nos. 5,539,082, 6,357,163, 6,710,163, 6,265,559 and 6,133,444).

A non-nucleophilic base that is strong enough to abstract a proton from the substituted or unsubstituted 3-aminopyrazole-4-carbonitrile can be used. If the alkylating agent is a carboxylic acid (e.g. compound I) and not the ester of the carboxylic acid (e.g. compound II), at least two equivalents of base should be used in the alkylation reaction for each equivalent of carboxylic acid. The base can be organic or inorganic. Non-limiting examples of such non-nucleophilic bases include: sodium hydride, potassium hydride, sodium carbonate, potassium carbonate, potassium tert-butoxide, triethylamine and N,N-diisopropylethylamine.

The solvent can be chosen such that the substituted or unsubstituted 3-aminopyrazole-4-carbonitrile is at least sparingly soluble. The 3-aminopyrazole-4-carbonitrile can be more soluble as increased solubility will facilitate faster reaction. The solvent should be aprotic to thereby avoid preferential deprotonation of the solvent over deprotonation of the substituted or unsubstituted 3-aminopyrazole-4-carbonitrile under basic conditions. Non-limiting examples of polar aprotic solvents include N-methyl-pyrrolidinone (NMP) and N,N-dimethylformamide (DMF). Other polar aprotic solvents are known to those of skill in the art. Suitable solvents can be selected by the ordinary practitioner by applying routine experimentation and the description provided herein.

Thus, in some embodiments, this invention pertains to a method comprising alkylating a substituted or unsubstituted 3-aminopyrazole-4-carbonitrile with a halo acetate moiety of the formula:

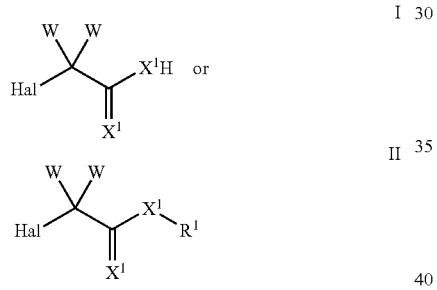

wherein the groups W, Hal, $X^1$ and $R^1$ are previously defined. In some embodiments, each W can be independently hydrogen, methyl, ethyl, n-propyl, isopropyl, n-butyl, isobutyl, tert-butyl or sec-butyl. In some embodiments, the group $R^1$ can be methyl, ethyl, n-propyl, isopropyl, n-butyl, isobutyl, tert-butyl, sec-butyl, allyl, trimethylsilyl, tert-butyldimethylsilyl or phenyl. In some embodiments, $R^1$ can be isobutyl, tert-butyl or sec-butyl. In some embodiments, $R^1$ can be allyl, trimethylsilyl, tert-butyldimethylsilyl or phenyl.

According to the method, at least one of the products of the alkylation reaction can be a substituted or unsubstituted heterocyclic compound of the formula:

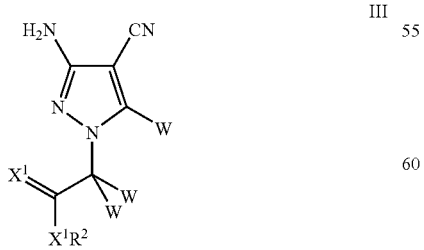

wherein W and $X^1$ are previously defined. The group $R^2$ can be hydrogen or $R^1$, wherein $R^1$ is previously defined. In some embodiments, the substituted or unsubstituted heterocyclic compound (compound III) can be isolated from other alkylation products of the reaction by crystallization or by other methods such as by chromatography.

If the alkylation is performed with a halo acetic acid (e.g. compound I), the product can either by isolated in the basic salt form or the product can be acidified to thereby regenerate the zwitterionic form or the amine protonated carboxylic acid form.

For those compounds that are alkylated with a halo acetic acid (e.g. compound I), the carboxylic acid group can be converted to an ester using known esterification procedures. For example, various procedures for forming esters can be found in Green et al., Protecting Groups In Organic Synthesis, Third Edition, John Wiley & Sons, Inc. New York, 1999.

Procedures for the production of some specific compounds of the general formula III can be found in the examples section below and in the figures.

ii) Nucleobase Formation

The following procedure is discussed with respect to the conversion of esters of N-1 alkylated substituted or unsubstituted 3-aminopyrazole-4-carbonitrile compounds (e.g. compound III) to N-8 alkylated substituted or unsubstituted 8-aza-7-deazaadenine. Said esters of the pyrazole can be prepared as described above under the heading "Alkylation".

Esters (including thioesters) of the alkylated substituted or unsubstituted 3-aminopyrazole-4-carbonitrile compounds having the formula:

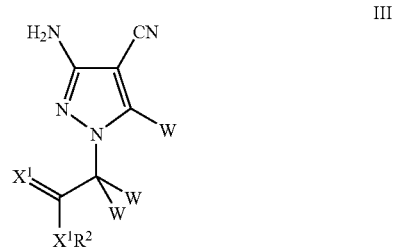

can be reacted with a substituted or unsubstituted diamine of the formula:

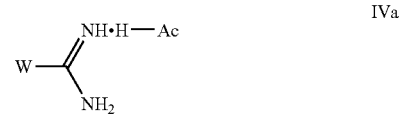

or a substituted or unsubstituted compound of the formula:

to thereby produce N-8 alkylated substituted or unsubstituted 8-aza-7deazaadenine compounds. Said N-8 alkylated substituted or unsubstituted 8-aza-7deazaadenine compounds can be protected and deprotected as appropriate and then used in the production of PNA oligomers comprising a substituted or unsubstituted 8-aza-7deazaadenine nucleobase. For the three structures set forth above, the groups W, $X^1$ and $R^1$ are previously defined. The group W' can be hydrogen or —$NH_2$.

By reference to substituted or unsubstituted with respect to the diamine (i.e. compound IVa), we refer to the group W as either hydrogen (unsubstituted) or another substituent (substituted). The group H—Ac is an acidic group capable of protonating the diamine. Compound VIa can produced from the diamine by adding an equivalent of acid to the diamine. The acidic group can be acetic acid. The acid group can be HCl or HBr. The acidic group can be another acid with a pK suitable for the protonation of the amine.

If compound IVa is used, the reaction can proceed in an alcohol-based solvent such as methanol, ethanol, n-propanol, isopropanol or tert-butanol. The reaction can proceed in other polar solvents such as N,N-dimethylformamide (DMF) or dimethylsulphoxide (DMSO).

If compound IVb is used, the reaction can, in some embodiments, proceed using compound IVb as a solvent. In some embodiments, a polar solvent (e.g. an alcohol) can be used.

Regardless of whether compound IVa or IVb is used, compound III should at least be sparingly soluble under the reaction conditions but can be very soluble or completely soluble in the chosen solvent. The more soluble, the faster the reaction will proceed. The reaction can be heated to increase the reaction rate and the solubility of compound III in the solvent. In some embodiments, the reaction is allowed to reflux in the chosen solvent. The specific conditions for the reaction, based upon the starting materials used, can be determined by the ordinary practitioner by the exercise of routine experimentation in accordance with the guidance set forth herein.

Thus, in some embodiments, this invention pertains to a method comprising reacting a substituted or unsubstituted heterocyclic compound of the formula:

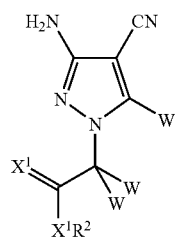

III with a substituted or unsubstituted diamine of the formula:

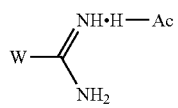

IVa or a substituted or unsubstituted compound of the formula:

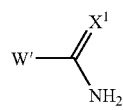

IVb wherein, W, W', $X^1$, $R^1$ and H—Ac are previously defined. In some embodiments, the method can be performed at reflux. In some embodiments, the solvent can be compound IVb, ethanol, propanol, isopropanol, tert-butanol, DMF or DMSO. In some embodiments, $R^1$ can be isobutyl, tert-butyl or sec-butyl. In some embodiments, $R^1$ can be allyl, trimethylsilyl, tert-butyldimethylsilyl or phenyl. In some embodiments, each $X^1$ is O.

In some embodiments, the reaction produces a substituted or unsubstituted heterocyclic compound of the formula:

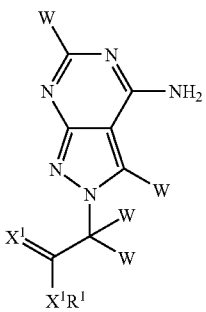

V wherein W, $X^1$ and $R^1$ are previously defined.

In some embodiments, the method can further comprise protecting the exocyclic amine of the substituted or unsubstituted heterocyclic compound with an amine-protecting group. Said protected substituted or unsubstituted heterocyclic compound can have the formula:

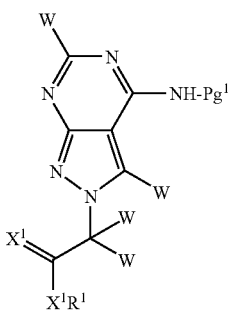

wherein the groups W, $X^1$, $R^1$ and $Pg^1$ are previously defined.

Protecting groups and methods for the production of protected amine groups are known in the art and exemplary procedures for said production can be found in Green et al., Protecting Groups In Organic Synthesis, Third Edition, John Wiley & Sons, Inc. New York, 1999.

Other known methods for the protection of exocyclic amine groups of nucleobases that can also be applied to the protection of the exocyclic amine group of said substituted or unsubstituted heterocyclic compound can be found in U.S. Pat. Nos. 6,063,569, 6,172,226 and 6,133,444. As described therein, generally the exocyclic amine can be reacted with a carbonyl equivalent (e.g. carbonyldiimidazole (CDI), phosgene, diphosgene or triphosgene) and the imidazolide or isocyanate can then be reacted with an alcohol (e.g. a substituted or unsubstituted 9-fluorenemethanol, diphenylmethanol (benzhydrol), benzyl alcohol, tert-butanol, or 3-hydroxypropionitrile) to thereby produce the amine protected as a carbamate.

For example, the amino protecting group can be Fmoc, Bhoc, Z, t-boc or Cyoc, wherein the Fmoc, Bhoc, Z, t-boc or Cyoc protecting groups can be substituted or unsubstituted. Accordingly, as referred to herein, the Fmoc, Bhoc, Z, t-boc or Cyoc protecting groups can have the following generic formulas:

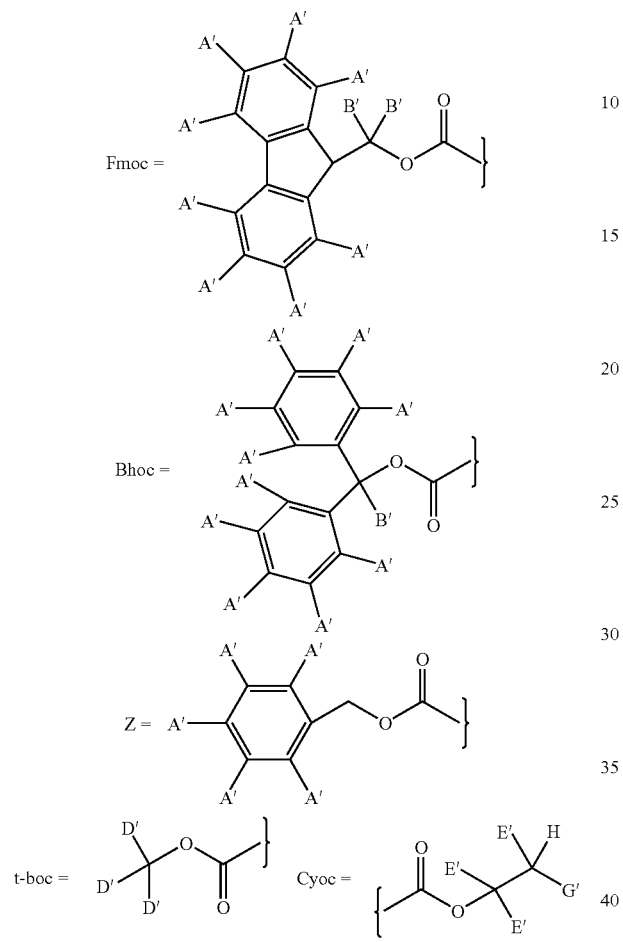

wherein each A' is independently hydrogen, fluorine, chlorine, bromine, iodine, methyl, ethyl, methoxy or ethoxy. Each B' is independently hydrogen, methyl or ethyl. Each D' is independently, methyl, trifluormethyl or ethyl. Each E' is independently hydrogen, methyl, ethyl, n-propyl, isopropyl, n-butyl, sec-butyl, iso-butyl or tert-butyl. H is hydrogen and G' is an electron withdrawing group. For example G' can be —CN or —NO$_2$. As illustrated, the bracket ")" illustrates the point of attachment of the protecting group to the exocyclic amine of nucleobase (e.g. Pg$^1$ in compound VI).

Whether or not the exocyclic amine is protected, the ester can be converted to a carboxylic acid group that can be used to link the protected or unprotected nucleobase to a PNA synthon or PNA oligomer. Conversion of the ester to a carboxylic acid group can be accomplished under either basic or acidic conditions depending on the nature of the ester and any protecting group on the nucleobase. Since an ester can be considered a protecting group, procedures for the basic or acid conversion of an ester to a carboxylic acid group can be found in Green et al., Protecting Groups In Organic Synthesis, Third Edition, John Wiley & Sons, Inc. New York, 1999.

Thus, in some embodiments the method can further comprise converting the ester of the unprotected compound (V) to a carboxylic acid or thiocarboxylic acid group to thereby produce an unprotected substituted or unsubstituted heterocyclic compound of the formula:

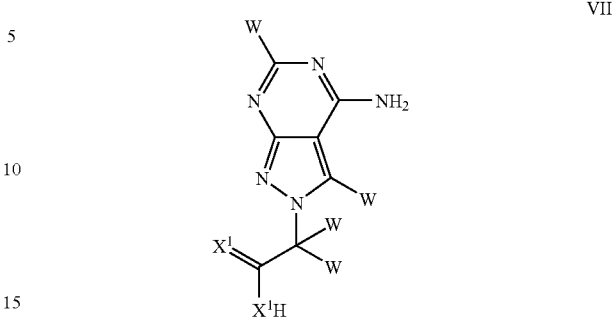

wherein, W and X$^1$ are previously defined. This unprotected substituted or unsubstituted heterocyclic compound (VII) comprises the 8-aza-7-deazaadenine nucleobase. The exocyclic amine of 8-aza-7-deazaadenine can be protected with an amine-protecting group and the partially protected heterocycle can then be used to produce PNA synthons (monomers) that can be used in PNA oligomer synthesis. The partially protected heterocycle can also be linked directly to the backbone of a PNA oligomer wherein the substituted or unsubstituted N-(2-aminoethyl)glycine moiety is a PNA subunit of a PNA oligomer or PNA/DNA Chimera (See: Example 11).

Moreover, in some embodiments, the method can further comprise converting the ester of the protected substituted or unsubstituted heterocyclic compound (VI) to a carboxylic acid or thiocarboxylic acid group to thereby produce a partially protected substituted or unsubstituted heterocyclic compound of the formula:

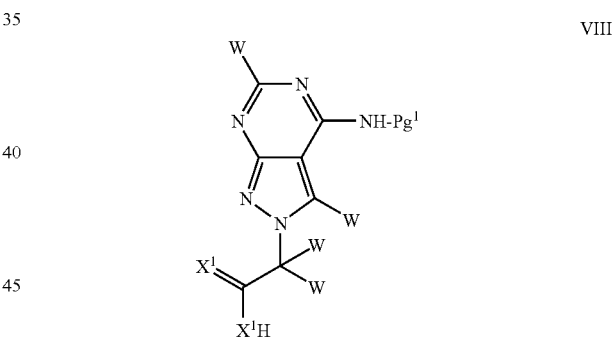

wherein, W, Pg$^1$ and X$^1$ are previously defined. In some embodiments, Pg$^1$ is Fmoc, Bhoc, Z, t-boc or Cyoc. These partially protected heterocyclic compounds comprise the 8-aza-7-deazaadenine nucleobase and are suitable for producing PNA synthons (monomers) that can be used in PNA oligomer synthesis. The partially protected heterocyclic compound can also be linked directly to the backbone of a PNA oligomer (See: Example 11).

Procedures for the production of specific compounds of the general formula V, VI, VII or VIII can be found in the examples section below and in the figures.

iii) PNA Synthon Production

PNA synthons (sometimes referred to as PNA monomers) are the basic building blocks used to assemble PNA oligomers. Methods, composition and instrumentation for the assembly of PNA oligomers are commercially available.

Various of the previously described partially protected substituted or unsubstituted heterocyclic compounds comprising the 8-aza-7-deazaadenine nucleobase (e.g. compound VIII)

can be used in the production of unique PNA monomers suitable for assembling PNA oligomers comprising one or more 8-aza-7-deazaadenine nucleobases as a universal base.

In some embodiments, the carboxylic acid or thiocarboxylic acid group of the previously described partially protected substituted or unsubstituted heterocyclic compounds (I.e. compound VIII) can be activated and then the carbonyl or thiocarbonyl group can be reacted with the secondary nitrogen of a substituted or unsubstituted N-(2-aminoethyl)glycine moiety. In this way, the nucleobase-containing moiety can be linked to the N-(2-aminoethyl)glycine backbone moiety. Methods for the activation of carboxylic acid groups and thiocarboxylic acid groups for reaction with amine groups are known and often practiced in the peptide synthesis arts.

For example, a carbonyl or thiocarbonyl carbon of the carboxylic acid or thiocarboxylic acid group can be activated for reaction with a secondary amine group (or other nucleophile) of a N-(2-aminoethyl)glycine backbone moiety by formation of a mixed anhydride (e.g. see U.S. Pat. Nos. 6,133,444, 6,172,226, 6,265,559 and 6,451,968 as well as Examples 7 and 10). The carbonyl or thiocarbonyl carbon can also be activated for reaction with known peptide coupling reagents such as benzotriazole-1-yl-oxy-tirs-(dimethylamino)-phosphoniumhexafluorophosphate (BOP) in combination with N-hydroxybenzotriazole (HOBT)) or 1-hydroxy-7-azabenzotriazole (HOAt) or by reaction directly with O-benzotriazol-1-yl-N,N,N',N'-tetramethyluronium hexafluorophosphate (HBTU) or 2-(7-Aza-1H-benzotriazole-1-yl)-1,1,3,3-tetramethyluronium hexafluorophosphate (HATU).

In some embodiments, the carboxylic acid or thiocarboxylic acid group of the previously described partially protected substituted or unsubstituted heterocyclic compounds (I.e. compound VIII) can be converted to an active ester. Active esters are known in peptide synthesis and refer to certain esters that are easily reacted with an amine of an amino acid under conditions commonly used in peptide synthesis (For a discussion of active esters please see: Innovation And Perspectives In Solid Phase Synthesis, Editor: Roger Epton, SPCC (UK) Ltd, Birmingham, 1990). A commonly used form of an active ester is the N-hydroxysuccinimidyl (NHS) ester. The active ester can be reacted with the secondary nitrogen (i.e. the N-glycyl nitrogen) of a substituted or unsubstituted N-(2-aminoethyl)glycine moiety. In this way, the nucleobase-containing moiety can be linked to the N-(2-aminoethyl)glycine backbone moiety.

Accordingly, in some embodiments, this invention pertains to a method comprising reacting the carbonyl or thiocarbonyl carbon of a carboxylic acid group, thiocarboxylic acid group or active ester (including a thiolated active ester) group of a substituted or unsubstituted heterocyclic compound of the formula:

IX

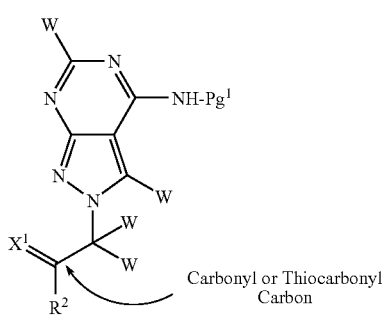

with the secondary nitrogen of a substituted or unsubstituted N-(2-aminoethyl)glycine moiety, wherein the groups W, $Pg^1$ and $X^1$ are previously defined. The group $R^2$ can be —OH, —SH or an active ester leaving group. For example the active ester leaving group can be:

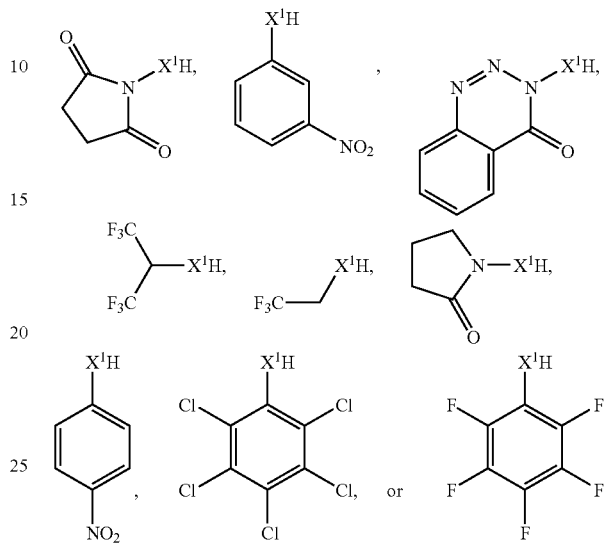

wherein $X^1$ is O or S.

In some embodiments, the substituted or unsubstituted N-(2-aminoethyl)glycine moiety can have the formula:

X

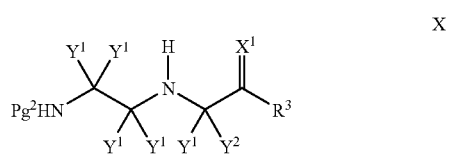

wherein, $Pg^2$ is an amine-protecting group and each $Y^1$ can be independently hydrogen, an alkyl group, alkenyl group, alkynyl group, heteroalkyl group, heteroalkenyl group, heteroalkynyl group, aryl group, heteroaryl group, arylalkyl group or heteroarylalkyl group. By substituted or unsubstituted N-(2-aminoethyl)glycine moiety, we refer to substitution of hydrogen at the groups identified as $Y^1$ and/or $Y^2$. Each group $Y^1$ can be independently hydrogen, an alkyl group, an alkenyl group, an alkynyl group, a heteroalkyl group, a heteroalkenyl group, a heteroalkynyl group, an aryl group, a heteroaryl group, an arylalkyl group or a heteroarylalkyl group. The group $Y^2$ can be hydrogen or a protected or unprotected amino acid side chain. The group $R^3$ can be —OH, —SH, $SR^1$ or —$OR^1$, wherein $R^1$ is previously defined. For example, $R^1$ can be methyl, ethyl, n-propyl, isopropyl, n-butyl, isobutyl, tert-butyl, sec-butyl, allyl, trimethylsilyl, tert-butyldimethylsilyl or phenyl.

$Pg^2$ can be an amine-protecting group different from $Pg^1$. $Pg^2$ can, independently from $Pg^1$, be Fmoc, Bhoc, Z, t-boc or Cyoc. Because the trityl group has also been used to protect the primary amine of the backbone of PNA monomers used in PNA oligomer synthesis (See: Vinayank et al., *Nucleosides and Nucleotides*, 16(7-9): 1653-1656 (1997)), $Pg^2$ can also be a substituted or unsubstituted trityl group of the formula:

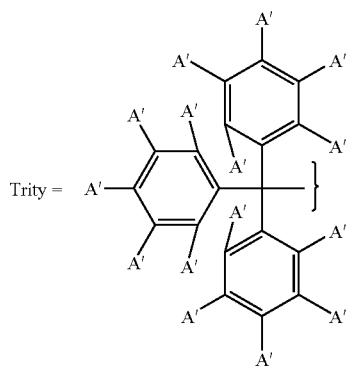

wherein A' is previously defined. The bracket "}" indicates the point of attachment.

Reaction of the carbonyl or thiocarbonyl carbon of the substituted or unsubstituted heterocyclic compound (I.e. compound VIII) with the secondary nitrogen of a substituted or unsubstituted N-(2-aminoethyl)glycine moiety links the partially protected substituted or unsubstituted nucleobase moiety to the backbone moiety of the PNA monomer, PNA oligomer or PNA/DNA Chimera, depending upon the nature of the substituted or unsubstituted N-(2-aminoethyl)glycine moiety.

The general procedure for the production of PNA synthons, wherein a partially protected alkylated nucleobase is coupled to a partially protected backbone subunit, is known (See: U.S. Pat. Nos. 5,539,082, 6,063,569, 6,172,226 and 6,133,444). Various solvents and conditions have been employed to thereby produce PNA monomers by this method. As the examples section below demonstrates (e.g. Examples 7 and 10), these conditions can be applied to the production of PNA synthons comprising the 8-aza-7-deazaadenine nucleobase by the exercise of routine experimentation in combination with the disclosure provided herein once the appropriate partially protected nucleobase (e.g. compound IX) is available.

Consequently, in some embodiments, the PNA synthons produced by the practice of this method can have the general formula:

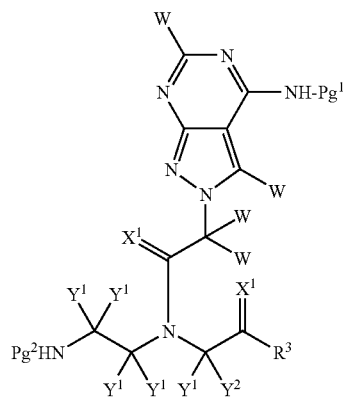

XI wherein $Y^1$, $Y^2$, W, $R^3$, $Pg^1$ and $Pg^2$ are previously defined. Each $X^1$ can be independently O or S.

Procedures for the production of specific PNA monomers of the general formula XI can be found in the examples section below and in the figures.

iv) Combinations

In some embodiments, this invention pertains to practicing two or more of the above described methods in combination. For example, in some embodiments, this invention pertains to practicing some or all aspects of the "Alkylation" method described above in combination with some or all aspects of the "Nucleobase Formation" method described above. In some embodiments, this invention pertains to practicing some or all aspects of the "Nucleobase Formation" method described above in combination with some or all aspects of the "PNA Synthon Production" method described above. In various embodiments, this invention also pertains to practicing some or all aspects of the "Alkylation" method described above in combination with some or all aspects of the "Nucleobase Formation" method described above in further combination with some or all aspects of the "PNA Synthon Production" method described above.

b. Compositions:

In some embodiments, this invention also pertains to certain compositions comprising 8-aza-7-deazaadenine, including intermediates for the production of said compositions.

Thus, in some embodiments, this invention pertains to a substituted or unsubstituted heterocyclic compound of the formula:

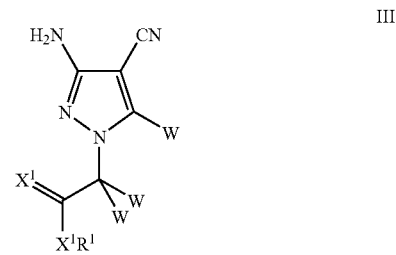

III wherein, the groups W, $R^1$ and $X^1$ are previously defined, provided that $R^1$ is not ethyl. For example, $R^1$ can be methyl, n-propyl, isopropyl, n-butyl, isobutyl, tert-butyl, sec-butyl, allyl, trimethylsilyl, tert-butyldimethylsilyl or phenyl. In some embodiments, $R^1$ can be isobutyl, tert-butyl or sec-butyl. In some embodiments, $R^1$ can be allyl, trimethylsilyl, tert-butyldimethylsilyl or phenyl. In some embodiments each $X^1$ can be O. Said substituted or unsubstituted heterocyclic compound can be produced by alkylation of 3-aminopyrazole-4-carbonitrile as previously described herein under the subheading: "Alkylation".

In various embodiments, this invention also pertains to a substituted or unsubstituted heterocyclic compound of the formula:

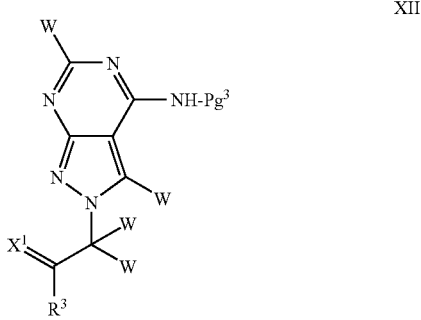

XII wherein, the groups W, $X^1$ and $R^3$ are previously defined. The group $Pg^3$ can be hydrogen or an amine-protecting group. For example, the amine-protecting group can be Fmoc, Bhoc, Z, t-boc or Cyoc. In some embodiments, $R^3$ can be —$SR^1$ or —$OR^1$, wherein $R^1$ is previously defined. For example, $R^1$ can be methyl, ethyl, n-propyl, isopropyl, n-butyl, isobutyl, t-butyl, sec-butyl, allyl, trimethylsilyl, t-butyldimethylsilyl or phenyl. In some embodiments, $R^1$ can be isobutyl, tert-butyl or sec-butyl. In some embodiments, $R^1$ can be allyl, trimethylsilyl, tert-butyldimethylsilyl or phenyl. In some embodiments, $X^1$ can be O.

Said substituted or unsubstituted heterocyclic compound can be produced by reacting an alkylated 3-aminopyrazole-4-carbonitrile (i.e. compound IIIa) with a diamine (i.e. compound IVa) or a compound of formula IVb as previously described under the subheading: "Nucleobase Formation".

In some embodiments, the substituted or unsubstituted heterocyclic compound can have the formula:

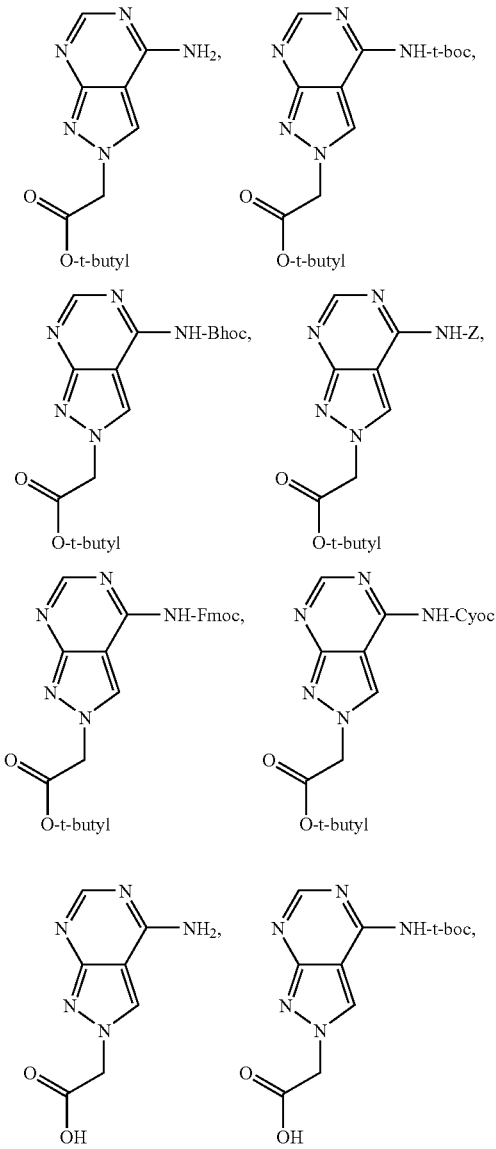

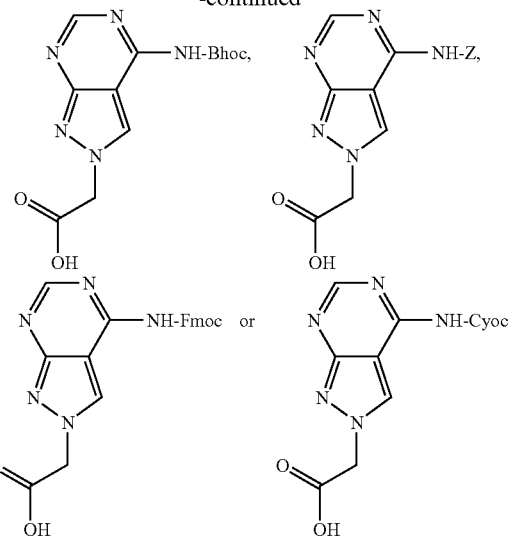

wherein the compound is optionally substituted.

In some embodiments, this invention also pertains to a PNA synthons of the formula:

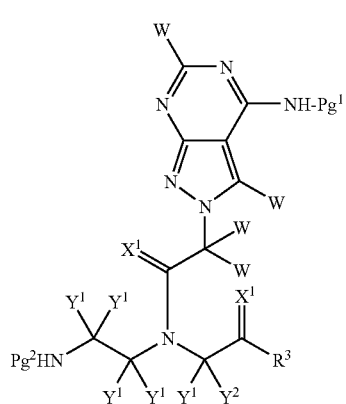

XI wherein $Y^1$, $Y^2$, W, $R^3$, $Pg^1$ and $Pg^2$ are previously defined. Each $X^1$ can be independently O or S. Said PNA synthons can be produced as previously described under the subheading: "PNA Synthon Production". Non-limiting examples of PNA synthons of interest can be found in FIGS. 7A and 7B.

6. EXAMPLES

Aspects of the present teachings can be further understood in light of the following examples, which should not be construed as limiting the scope of the present teachings in any way.

Example 1

Synthesis of 3-Amino-4-cyano-pyrazolo-N1-t-Butyl acetate (1A)

To a solution of 3-aminopyrazole-4-carbonitrile (25.00 g, 0.23 mole, Lancaster, USA, P/N 7086) in N,N-dimethylformamide (DMF, 150 mL) was added potassium carbonate (48.39 g, 0.35 mole, Aldrich Chemical, Milwaukee, Wis., USA, P/N 34782). The reaction mixture was stirred at room temperature for 30 minutes (min) and then bromo-tertiarybutyl acetate (41.4 mL, mole, Aldrich chemical, Milwaukee, Wis., USA, P/N 124230) was added slowly. The reaction mixture was stirred at room temperature for an additional 2 hours (h). The reaction mixture was then filtered and was evaporated to dryness. The crude mixture was dissolved in dichloromethane (1.5 L) and the organic layer was washed with water (1.0 L) and then with 5% NaCl solution. The organic layer was separated dried over sodium sulfate and evaporated. Crystallization of the crude mixture with dichloromethane yielded the 3-amino-4-cyano-pyrazole-N2-t-butyl acetate (1B) while the mother liquor gave the 3-amino-4-cyanopyrazole-N1-t-butyl acetate (1A). Yield of compound 1A was 20.65 g (41%). $^1$H-NMR of Compound IA $^1$H-NMR (DMSO-$d_6$): δ 1.47 (s, 9H), 4.69 (s, 2H), 5.98 (s, 2H), 8.06 (s, 1H).

Example 2

Synthesis of 6-amino-pyrazolo[3,4-d]pyrimidine-$N^8$-t-butyl acetate (2)

3-Amino-4-cyanopyrazole-$N^1$-t-butyl acetate (1A) (3.0 g, 13.6 mmol) was dissolved in absolute ethanol (150 mL, Aldrich Chemical, Milwaukee, Wis., USA) and then formamidine acetate (4.0 g, 20.18 mmol, Aldrich Chemical, Wisconsin, USA, P/N 15803) was added. The reaction mixture was heated to reflux for 14 hours, filtered and evaporated to dryness. The residue was purified by flash silica gel column. The product was eluted with 2-6% methanol in dichloromethane. The appropriate fractions were collected and evaporated. Yield 1.53 g (75%).

$^1$H-NMR (DMSO-$d_6$): δ 1.42 (s, 9H), 5.24 (brs, 2H), 8.13 (s, 1H), 8.34 (d, 1H, J=2.34 Hz).

Example 3

Synthesis of $N^6$-benzyloxycarbonyl-pyrazolo[3,4-d]-pyrimidine-$N^8$-yl-t-butyl acetate (3)

6-Amino-pyrazolo[3,4-d]pyrimidine-N8-yl-tBu acetate (2) (8.52 g, 32.02 mmol) was suspended in dry N,N-dimethylformamide (DMF, 85 mL) and the mixture was stirred under argon. To this mixture was added 1,1-carbonyldiimidazole (CDI, 7.8 g, 48.4 mmol, Aldrich Chemical, Milwaukee, Wis., USA, P/N 115533) and the reaction mixture was stirred at the temperature between 95-103° C. After two hours, the temperature was lowered to 75° C., benzyl alcohol (5.0 mL, 44.45 mmol, Aldrich Chemical, Milwaukee, Wis., USA, P/N 305197) was added and then the oil bath was removed. The mixture was stirred at room temperature overnight and then evaporated to dryness. The crude residue was dissolved in ethyl acetate (1.2 L), washed with water (1.5 L) and with 5% (wt/v) sodium chloride in water. The organic layer was separated, dried over sodium sulphate, filtered and evaporated. The product was crystallized from a mixture of dichloromethane and acetonitrile (9:1 v/v). Yield 8.25 g (63%).

$^1$H-NMR (DMSO-$d_6$): δ 1.43 (s, 12H), 5.25 (s, 2H), 5.34 (s, 2H), 7.34-7.46 (m, 5H), 8.53 (s, 1H), 8.86 (s, 1H), 11.35 (brs, 1H).

Example 4

Synthesis of $N^6$-benzyloxycarbonyl-pyrazolo[3,4-d] pyrimidine-$N^8$-acetic acid $N^6$-Benzyloxycarbonyl-pyrazolo[3,4-d]pyrimidine-$N^8$-yl-tBu acetate (3) (2.65 g, 10.63 mmol) was dissolved in dry dichloromethane (65 mL) and treated with triethylsilane (13.73 g, 118 mmol, Aldrich Chemical, Milwaukee, Wis., USA, P/N 230197). The reaction mixture was cooled to 0° C. in ice-bath and trifluoacetic acid (30 mL) was added over a period of 15 minutes. The reaction mixture was stirred at 0° C. for 10 minutes and slowly the temperature increased to 25° C., and stirred for 8 hours. The reaction mixture was evaporated to dryness and the residue co-evaporated with dichloromethane (3×30 mL). The product was crystallized from a mixture of dichloromethane and ether (9:1 v/v). Yield 1.98 g (97%).

$^1$H-NMR (DMSO-$d_6$): δ 5.27 (s, 2H), 5.38 (s, 2H), 7.35-7.48 (m, 5H), 8.54 (s, 1H), 8.89 (s, 1H), 10.98 (brs, 1H), 11.92 (brs, 1H).

Example 5

Synthesis of N'-([6-[N-benzyloxycarbonyl]pyrazolo[3,4-d]pyrimidine-$N^8$-acetyl-N"-(2-t-butyloxycarbonyl]-2-aminoethyl)glycine ethyl ester (5)

To (3.60 g, 10.99 mmol) of N6-benzyloxycarbonyl-pyrazolo[3,4-d]pyrimidine-N8-acetic acid (4) was added anhydrous N,N-dimethylformamide (DMF, 45.0 mL) and the mixture was stirred under argon. To this mixture was added a solution of $N^1$-(tert-butoxycarbonyl)-$N^4$-(2-aminoethyl)-glycine ethyl ester (2.71 g, 10.98 mmol) in N,N-dimethylformamide (5.0 mL). To this reaction mixture was added BOP (12.16 g, 27.5 mmol, Novabiochem, Merck Biosciences AG, Germany, P/N A3184a), HOBT (3.72 g, 27.47 mmol, Novabiochem, Merck Biosciences AG, Darmstadt, Germany, P/N 01-62-008) and N,N-diisopropylethylamine (4.5 mL, Aldrich Chemical Milwaukee, Wis., USA, P/N 387649). The reaction mixture was stirred at room temperature for 8 hours and then evaporated. The residue was dissolved in dichloromethane (600 mL) and washed with sodium bicarbonate solution (500 mL). The organic layer was dried with sodium sulphate, filtered and evaporated and co-evaporated with toluene (3×25 mL). The product was purified on flash silica gel column and was eluted with approx 5-12% (v/v) ethylacetate in dichloromethane). Yield 4.65 g (76%).

$^1$H-NMR (DMSO-$d_6$): δ 1.17 (t, 3H), 1.17 (s, 9H), 3.22-3.46 9 m, 4H), 4.14 (m, 2H), 4.21 (q, 2H), 4.32 (s, 2H), 5.26 (s, 2H), 7.39-7.45 (m, 5H), 8.52 (s, 1H), 8.77 (d, 1H, J=2.13 Hz), 10.48 (brs, 1H).

Example 6

Synthesis of N'-([6-[N-benzyloxycarbonyl]pyrazolo[3,4-d]pyrimidine-$N^8$-acetyl)-N"-(2-[tert-butyloxycarbonyl]-2-aminoethyl)-glycine (6)

N'-([6-[N-benzyloxycarbonyl]pyrazolo[3,4-d]pyrimidine-N-8-acetyl)-N"-(2-[tert-butyloxycarbonyl]-2-aminoethyl)-glycine ethyl ester (6) (2.0 g, 3.61 mmol) was dissolved in a mixture of acetonitrile (30 mL) and N,N-dimethylformamide (10 mL), and the reaction mixture cooled to 0° C. in ice-bath. To this mixture was added a 2M solution of lithium hydroxide (10 mL) and the reaction mixture was stirred at 0° C. After 20 min, 2N hydrochloric acid (10 mL) was added.

The final pH was ~3. The solvent was completely evaporated in vacuo, co-evaporated with toluene (2×25 mL) and then co-evaporated with acetonitrile (2×25 mL). The product was crystallized from water. Cold water (10 mL) was added to residue and solid was collected by filtration. Yield 1.92 g (95%).

$^1$H-NMR (DMSO-$d_6$): δ 1.39 (s, 9H), 3.12-3.44 (m, 4H), 4.29 (s, 2H), 5.34 (s, 2H), 5.63 (s, 2H), 7.35-7.47 (m, 5H), 8.52 (s, 1H), 8.77 (d, 1H, J=2.98 Hz), 10.98 (brs, 1H), 12.5 (brs, 1H).

Example 7

Synthesis of N—[N"-fluorenylmethyloxycarbonyl-(2"-aminoethyl)]-N-[2-$N^6$-benzyloxycarbonyl]pyrazolo[3,4-d]pyrimidine-$N^8$-acetyl]glycine (7)

To 0.5 g (1.53 mmol) of N6-benzyloxycarbonyl-pyrazolo[3,4-d]pyrimidine-N8-acetic acid (4) in 20 mL of acetonitrile was added in one portion of 300 μL (3.13 mmol) of N-methylmorpholine at room temperature and the resulting mixture was stirred at room temperature for 10 minutes. The mixture was cooled to 0° C., and pivaloyl chloride (210 μL, 1.68 mmol) was added dropwise under argon. The reaction mixture was stirred at room temperature for 20 minutes. In a separate flask, 0.5 g (1.46 mmol) of finely grounded N—[N'-fluorenylmethylloxycarbonyl-(2'-aminoethyl)]glycine was suspended in 20 mL of a mixture of acetonitrile/water (1:1). Sodium carbonate (100 mg) was added and the resulting mixture was stirred for 10 minutes. The two solutions were then combined and the resulting mixture stirred for 30 minutes at room temperature. The solvents were removed by evaporation and the residue was dissolved in dichloromethane (150 mL) and washed with sodium chloride solution (300 mL). The organic layer was dried with sodium sulphate and evaporated to dryness, in vacuo. The crude product was purified on flash silica gel column using methanol-dichloromethane 10-15% as eluent.

$^1$H-NMR (DMSO-$d_6$): δ 3.22-3.46 (m, 4H), 4.14 (s, 2H), 4.62 (m, 2H), 4.65-4.70 (m, 4H), 7.28-7.84 (m, 14H), 8.65 (s, 1H), 8.88 (s, 1H), 10.58 (brs, 1H), 12.43 (brs, 1H).

Example 8

Synthesis of $N^6$-benzhydroxycarbonyl-pyrazolo[3,4-d]pyrimidine-$N^8$-yl t-Butyl acetate (8)

To 6-aminopyrazolo[3,4-d]pyrimidine-$N^8$-t-Butyl acetate (2) (5.0 g, 20.05 mmol) in dry N,N-dimethylformamide (80 mL) was added 1,1-carbonyldi-imidazole (5.0 g, 30.63 mmol). The reaction mixture was slowly heated to 103° C. under argon, and then maintained the temperature for 2 hours. The temperature of the oil bath was reduced to 75° C., and then benzhydrol (6.25 g, 33.92 mmol) was added to the reaction mixture. All heat was removed and the reaction was allowed to stir at room temperature overnight. The reaction mixture was evaporated in vacuo and the crude mixture was dissolved in dichloromethane (1L) and washed with 5% sodium chloride solution. The organic phase was separated, dried over sodium sulphate, filtered and evaporated to dryness. The product was purified by flash silica gel column. The product was eluted using 6-10-[% v/v] of ethyl acetate in dichloromethane. The appropriate fractions were collected and evaporated. Yield 6.89 g (74.7%).

$^1$H-NMR (DMSO-$d_6$): δ 1.41 (s, 9H), 5.32 (s, 2H), 6.85 (s, 1H), 7.26-7.49 (m, 10H), 8.54 (s, 1H), 8.82 (d, 1H, J=3.5 Hz), 11.52 (brs, 1H).

Example 9

Synthesis of $N^6$-benzhydroxycarbony-pyrazolo[3,4-d]pyrimidine-$N^8$-yl acetic acid (9)

To 2.00 g (4.35 mmol) of $N^6$-benzhydroxycarbonyl-pyrazolo[3,4-d]pyrimidine-$N^8$-yl t-Butyl acetate (8) was added ethanol (60 mL) and acetonitrile. The reaction mixture was cooled in ice bath to less than 5° C. To this mixture was added 1.93 g of lithium hydroxide dissolved in 20 mL of water and the temperature rose to 25° C. The reaction mixture was stirred for 15 minutes, cooled to 0° C. and then a 2M solution of citric acid in water (pH ~3) was added. The reaction mixture was evaporated to dryness and the residue was triturated with cold water. The product was crystallized from methanol. Yield 1.65 (82.62%).

$^1$H-NMR (DMSO-$d_6$): δ 5.30 (s, 2H), 6.84 (s, 1H), 7.21-7.49 (m, 10H), 8.52 (s, 1H), 8.79 (s, 1H), 10.89 (s, 1H), 11.92 (s, 1H).

Example 10

Synthesis of N—[N"-fluorenylmethyloxycarbonyl-(2"-aminoethyl)]-N-[(2-$N^6$-bennzhydroloxycarbonyl-$N^8$-pyrazolo[3,4-d]pyrimidine)]acetyl]glycine or N—[N"-Fmoc-(2"-aminoethyl)]-N-[2-[N6-Bhoc-(pyrazolo[3,4-d]pyrimidine-$N^8$-yl)]acetyl glycine (10)

To 1.0 g (2.47 mmol) of $N^6$-benzhydroxycarbony-pyrazolo[3,4-d]pyrimidine-$N^8$-yl acetic acid (9) in 10 mL of dry acetonitrile was added 560 μL of N-methylmorpholine. The reaction mixture was stirred at room temperature for 10 minutes. The reaction mixture was then cooled to 0° C. and was pivaloyl chloride 310 μL, 2.59 mmol) added under argon for 30 minutes. In a separate flask 0.87 g (2.45 mmol) of N—[N'-fluorenylmethyloxycarbonyl-(2'-aminoethyl)]glycine was suspended in a mixture of acetonitrile (10 mL), water (5 mL), sodium carbonate (0.76 g) and potassium carbonate (0.65 g). The suspension was stirred at room temperature until a clear solution was obtained. The reaction mixture of pivaloyl activated ester of $N^6$-benzhydroxycarbony-pyrazolo[3,4-d]pyrimidine-$N^8$-yl acid was then added to the solution of N—[N'-fluorenylmethyloxycarbonyl-(2'-aminoethyl)]glycine and then the reaction was stirred for 30 minutes at room temperature. The reaction mixture was evaporated to dryness, co-evaporated with toluene (2×20 mL) and purified on flash silica gel column. The column was eluted with 10-15% methanol in dichloromethane. Yield 280 mg (10%).

Example 11

Solid Phase Coupling of $N^6$-benzhydroxycarbonyl-pyrazolo[3,4-d]pyrimidine-$N^8$-yl acetic acid (9) to a PNA Oligomer With reference to FIG. 8A, N-[tert-butyloxycarbonyl]-[N'-fluorenylmethyloxycarbonyl-(2'-aminoethyl)]glycine (20) was coupled to a support bound PNA oligomer of the illustrated nucleobase sequence (21) to thereby form the fully protected support bound PNA oligomer (22). With reference to FIG. 8B, the Fmoc group of the fully protected support bound PNA oligomer (22) was then removed to form the partially deprotected support bound PNA oligomer (23). Then $N^6$-benzhydroxycarbonyl-pyrazolo[3,4-d]pyrimidine-$N^8$-yl acetic acid (9) was condensed with the secondary nitrogen (the N-glycyl nitrogen) of the terminal PNA backbone moiety of the support bound PNA oligomer (23) to thereby form the fully protected, elongated support bound PNA oligomer (24). This PNA oligomer was then cleaved from the support, deprotected and purified using conventional methods to thereby form the fully deprotected PNA oligomer (25) comprising a N8-8-aza-7deazaadenine nucleobase illustrated as U for universal base.

With the exception of the use of a novel partially protect N8-8-aza-7deazaadenine nucleobase, the synthesis of the PNA oligomer proceeded substantially as described by Seitz et al., Convergent strategies for the attachment of fluorescing reporter groups to peptide nucleic acids in solution and on solid phase, *Chemistry—A European Journal* (2001), 7(18), 3911-3925 or Seitz et al., A convergent strategy for the modification of peptide nucleic acids: novel mismatch-specific PNA-hybridization probes, *Angewandte Chemie*, International Edition (1999), 38(15), 2203-2206.

While the present teachings are described in conjunction with various embodiments, it is not intended that the present teachings be limited to such embodiments. On the contrary, the present teachings encompass various alternatives, modifications and equivalents, as will be appreciated by those of skill in the art.

7. REFERENCES

1. Challa et al., *Organic Letters*, 1(10): 1639-1641 (1999)
2. Coull et al., U.S. Pat. No. 6,172,226
3. Coull et al., U.S. Pat. No. 6,133,444
4. El Fahham, Hassan Attia, *Egyptian Journal of Pharmaceutical Sciences*, 33(34): 561-570 (1992)
5. Elnagdi et al. *Journal of Heterocyclic Chemistry*, 17(1) 73-76 (1980)
6. Hann et al., WO00/02899
7. Köhler et al., *Chem Bio Chem*, 6: 69-77 (2005)
8. Oliver et al., Abstract of Papers, 222$^{nd}$ ACS National Mtg., Chicago, Ill., Aug. 26-30 (2001)
9. Parton et al., U.S. Pat. No. 6,433,134
10. Pennell et al., US Patent Application Publication No. US2004/0162282 A1
11. Pennell et al., WO03/105853
12. Robbins, Roland, K., *J. Am. Chem. Soc.*, 78: 784-790 (1955)
13. Seela et al., *Nucleic Acids Research*, 28(17): 3224-3232 (2000)
14. Seela et al. *Helvetica Chemica Acta*, 83: 1437 (2000)
15. Seela et al., *Helvetica Chimica Acta*, 71: 1813 (1988)
16. Seitz et al. *Angewandte Chemie, International Edition*, 38(15): 2203-2206 (1999)
17. Seitz et al., *Chemistry—A European Journal*, 7(18): 3911-3925 (2001)
18. Thomson et al., *Tetrahedron*, 51(22): 6179 (1995)
19. Zhang et al., *Methods*, 23: 132-140 (2001)

We claim:

1. A method comprising:
a) alkylating a substituted or unsubstituted 3-aminopyrazole-4-carbonitrile compound with a halo acetate compound of the formula:

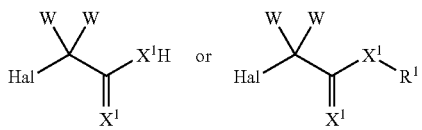

wherein,

W is hydrogen;

R$^1$ is an alkyl group, an alkenyl group, an alkynyl group, a heteroalkyl group, a heteroalkenyl group, a heteroalkynyl group, an aryl group, a heteroaryl group, an arylalkyl group or a heteroarylalkyl group;

Hal is Cl, Br or I; and each X$^1$ is O.

2. The method of claim 1, wherein R$^1$ is methyl, n-propyl, isopropyl, n-butyl, isobutyl, tert-butyl, sec-butyl, allyl, trimethylsilyl, tert-butyldimethylsilyl or phenyl.

3. The method of claim 1, wherein one of the products of the reaction is a substituted or unsubstituted heterocyclic compound of the formula:

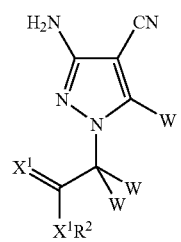

wherein,

W is hydrogen;

R$^1$ is hydrogen or an alkyl group, an alkenyl group, an alkynyl group, a heteroalkyl group, a heteroalkenyl group, a heteroalkynyl group, an aryl group, a heteroaryl group, an arylalkyl group or a heteroarylalkyl group; and X$^1$ is O.

4. A method comprising:
a) reacting a substituted or unsubstituted heterocyclic compound of the formula:

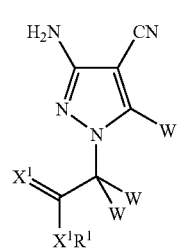

with a substituted or unsubstituted compound of the formula:

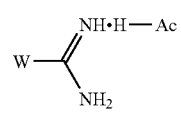

or a substituted or unsubstituted compound of the formula:

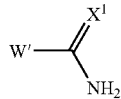

IVb wherein the reaction produces a substituted or unsubstituted heterocyclic compound of the formula:

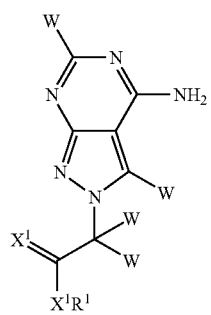

V wherein,
W is hydrogen;
W' is hydrogen or —NH₂;
$R^1$ is an alkyl group, an alkenyl group, an alkynyl group, a heteroalkyl group, a heteroalkenyl group, a heteroalkynyl group, an aryl group, a heteroaryl group, an arylalkyl group or a heteroarylalkyl group;
H—Ac is an acidic group capable of protonating the diamine; and
$X^1$ is O.

5. The method of claim 4, wherein the solvent for the reaction is compound IVb, methanol, ethanol, n-propanol, isopropanol or t-butanol, N,N-dimethylformamide (DMF) or dimethylsulphoxide (DMSO).

6. The method of claim 4, wherein the reaction is allowed to reflux.

7. The method of claim 4, further comprising:
b) protecting the exocyclic amine of the substituted or unsubstituted heterocyclic compound V with a amine protecting group to thereby produce a compound of the formula:

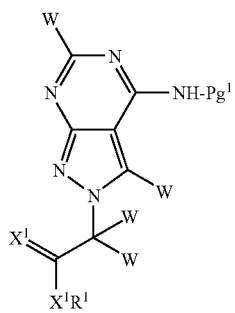

VI wherein,
W is hydrogen;
$Pg^1$ is an amine protecting group;
$R^1$ is an alkyl group, an alkenyl group, an alkynyl group, a heteroalkyl group, a heteroalkenyl group, a heteroalkynyl group, an aryl group, a heteroaryl group, an arylalkyl group or a heteroarylalkyl group; and
$X^1$ is O.

8. The method of claim 7, wherein the amine protecting group is Fmoc, Bhoc, Z, t-boc or Cyoc.

9. The method of claim 4, further comprising:
b) converting the ester group of compound V to a carboxylic acid group to thereby produce a substituted or unsubstituted heterocyclic compound of the formula:

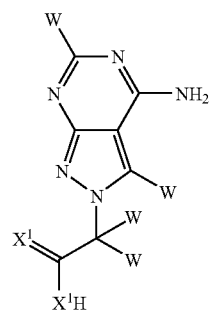

VII wherein,
W is hydrogen; and
$X^1$ is O.

10. The method of claim 7, further comprising:
c) converting the ester group of compound VI to a carboxylic acid group to thereby produce a substituted or unsubstituted heterocyclic compound of the formula:

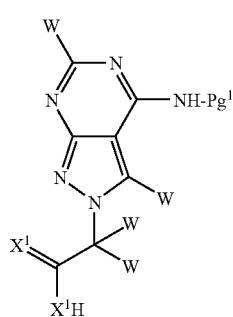

VIII wherein,
W is hydrogen;
$Pg^1$ is an amine protecting group; and
$X^1$ is O.

11. The method of claim 10, wherein $Pg^1$ is Fmoc, Bhoc, Z, t-boc or Cyoc.

12. A method comprising:
a) reacting the carbonyl carbon of the activated carboxylic acid group or active ester group of a substituted or unsubstituted heterocyclic compound of the formula:

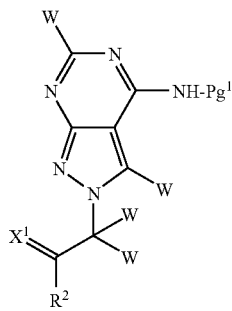

IX with the secondary nitrogen of a substituted or unsubstituted N-(2-aminoethyl)glycine moiety,
wherein,
W is hydrogen;
$Pg^1$ is an amine protecting group;
$R^2$ is —SH, —OH or an active ester leaving group; and
$X^1$ is O.

13. The method of claim 12, wherein the substituted or unsubstituted N-(2-aminoethyl)glycine moiety has the formula:

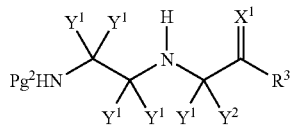

X wherein,
$Pg^2$ is an amine protecting group;
each $Y^1$ is independently hydrogen, an alkyl group, an alkenyl group, an alkynyl group, a heteroalkyl group, a heteroalkenyl group, a heteroalkynyl group, an aryl group, a heteroaryl group, an arylalkyl group or a heteroarylalkyl group;
$Y^2$ is hydrogen or a protected or unprotected amino acid side chain;
$R^3$ is —OH, —SH, —$SR^1$ or —$OR^1$, wherein $R^1$ is an alkyl group, an alkenyl group, an alkynyl group, a heteroalkyl group, a heteroalkenyl group, a heteroalkynyl group, an aryl group, a heteroaryl group, an arylalkyl group or a heteroarylalkyl group; and
$X^1$ is O.

14. The method of claim 13, wherein $R^1$ is methyl, ethyl, n-propyl, isopropyl, n-butyl, isobutyl, tert-butyl, sec-butyl, allyl, trimethylsilyl, tert-butyldimethylsilyl or phenyl.

15. The method of claim 12, wherein the substituted or unsubstituted N-(2-aminoethyl)glycine moiety is a PNA subunit of a PNA oligomer.

16. The method of claim 12, wherein, $Pg^1$ is Fmoc, Bhoc, Z, t-boc or Cyoc.

17. The method of claim 13, wherein $Pg^1$ is Fmoc, Bhoc, Z, t-boc or Cyoc and wherein $Pg^2$ is different from $Pg^1$ and $Pg^2$ is independently Fmoc, Bhoc, Z, t-boc, Cyoc or trityl.

18. The method of claim 12, wherein the active ester leaving group is a group of the formula:

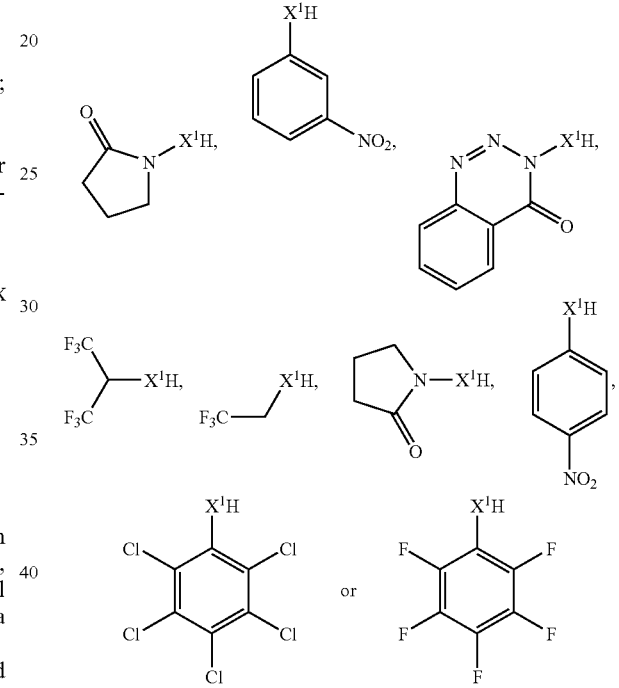

wherein $X^1$ is O.

* * * * *